(12) United States Patent
Reitz et al.

(10) Patent No.: US 6,858,636 B2
(45) Date of Patent: Feb. 22, 2005

(54) 1-PHENYL IMIDAZOL-2-ONE BIPHENYLMETHYL COMPOUNDS FOR TREATMENT OF CIRCULATORY DISORDERS

(75) Inventors: David B. Reitz, Chesterfield, MO (US); Robert E. Manning, St. Louis, MO (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 10/649,210

(22) Filed: Aug. 27, 2003

(65) Prior Publication Data

US 2004/0048911 A1 Mar. 11, 2004

Related U.S. Application Data

(63) Continuation of application No. 09/825,029, filed on Apr. 3, 2001, now Pat. No. 6,630,497, which is a continuation of application No. 09/625,770, filed on Jul. 26, 2000, now abandoned, which is a continuation of application No. 09/450,926, filed on Nov. 29, 1999, now abandoned, which is a continuation of application No. 09/239,443, filed on Jan. 28, 1999, now abandoned, which is a continuation of application No. 09/024,021, filed on Feb. 16, 1998, now abandoned, which is a continuation of application No. 08/787,841, filed on Jan. 23, 1997, now abandoned, which is a continuation of application No. 08/036,316, filed on Mar. 24, 1993, now abandoned.

(51) Int. Cl.$^7$ ................. A61K 31/4166; A61K 31/4178
(52) U.S. Cl. ...................... 514/381; 514/392; 548/252; 548/325.5
(58) Field of Search ............................ 548/252, 325.5; 514/381, 392

(56) References Cited

U.S. PATENT DOCUMENTS

| | | | | | |
|---|---|---|---|---|---|
| 5,087,634 | A | * | 2/1992 | Reitz et al. | ................. 514/381 |
| 5,238,952 | A | * | 8/1993 | Reitz et al. | ................. 514/381 |
| 6,630,497 | B2 | * | 10/2003 | Reitz et al. | ................. 514/381 |

* cited by examiner

*Primary Examiner*—Laura L. Stockton
(74) *Attorney, Agent, or Firm*—J. Timothy Keane

(57) ABSTRACT

A class of 1-phenyl imidazol-2-one biphenylmethyl compounds is described for use in treatment of circulatory disorders. Compounds of particular interest are angiotensin II antagonists of the formula

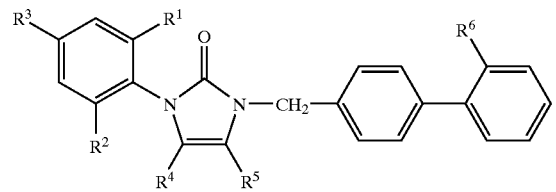

wherein each of $R^1$, $R^2$ and $R^3$ is independently selected from hydrido, alkyl, alkoxy, cyano, halo, hydroxy, carboxyl, alkoxycarbonyl, formyl and acetyl; alkylcarbonyl and haloalkylcarbonyl; with the proviso that at least one of $R^1$, $R^2$ and $R^3$ must be a substituent other than hydrido, and with the further proviso that when each of $R^1$ and $R^3$ is hydrido, then $R^2$ cannot be chloro; wherein $R^4$ is hydrido; wherein $R^5$ is alkyl; and wherein $R^6$ is tetrazolyl; or a stereoisomer or a tautomer thereof or a pharmaceutically-acceptable salt thereof. These compounds are particularly useful in treatment or control of hypertension and congestive heart failure.

9 Claims, No Drawings

1-PHENYL IMIDAZOL-2-ONE BIPHENYLMETHYL COMPOUNDS FOR TREATMENT OF CIRCULATORY DISORDERS

RELATED APPLICATIONS

This application is a continuation of application Ser. No. 09/825,029, filed on Apr. 3, 2001, now issued as U.S. Pat. No. 6,630,497 which is a continuation of application Ser. No. 09/625,770, filed Jul. 26, 2000, now abandoned, which is a continuation of application Ser. No. 09/450,926, filed on Nov. 29, 1999, now abandoned, which is a continuation of application Ser. No. 09/239,443, filed Jan. 28, 1999, now abandoned, which is a continuation of application Ser. No. 09/024,021, filed Feb. 16, 1998, now abandoned, which is a continuation of application Ser. No. 08/787,841, filed Jan. 23, 1997, now abandoned, which is a continuation of application Ser. No. 08/036,316, filed Mar. 24, 1993, now abandoned.

FIELD OF THE INVENTION

Non-peptidic 1-phenyl imidazol-2-one biphenylmethyl compounds are described for use in treatment of circulatory disorders such as hypertension and congestive heart failure. Of particular interest are angiotensin II antagonist compounds provided by imidazol-2-one compounds having a mono- or poly-substituted phenyl moiety attached to a nitrogen atom of the imidazole-2-one nucleus and having a biphenylmethyl moiety attached to other nitrogen atom of the imidazol-2-one nucleus.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247(1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 31–21 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on a triazole ring. For example, East German Patent No. 160,447 published 3 Aug. 1983 describes a family of 1,2,4-triazolin-5-one compounds, specifically 2,4-dihydro-4,5-bis(phenylmethyl)-3H-1,2,4-triazol-3-one, for use as herbicides. Belgian Patent No. 806,146 published 16 Oct. 1972 describes a family of triazolinone compounds, including the compound (3-(4-m-chlorophenyl-1-piperazinyl)-propyl)-3,4-diethyl-1,2,4-triazolin-5-one, having tranquilizer, hypotensive and analgesic activities. Belgian Patent No. 631,842 published 28 Feb. 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published 15 Jun. 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published 18 Mar. 1987 describes a family of $N^1$-diarylmethyl-$N^2$-aminoalkyl-diaza-heterocyclic derivatives for treating cerebral vascular and ischemic diseases and for protecting against anoxia.

There are several families of known compounds having an oxo group attached to a imidazole biphenylmethyl nucleus. For example, U.S. Pat. No. 5,177,097 to Poss describes acyl amidine and acyl guanidine biphenylmethyl compounds as angiotensin II antagonists, including imidazole-4-one-type biphenylmethyl compounds such as 4'-[[4,5-Dihydro-5-methyl-4-oxo-2-(propylamino)-1H-imidazol-1-yl]methyl]-[1,1'-biphenyl]-2-carboxylic acid, trifluoroacetate (1:1) salt. U.S. Pat. No. 5,087,634 to Reitz et al describes a class of N-substituted imidazole-2-one biphenylmethyl compounds as angiotensin II antagonists, including the compound 1-phenyl-4-butyl-1,3-dihydro-3-[2'-(1H-tetrazol-5-yl)[1,1'-biphenyl]-4-ylmethyl]-2H-imidazol-2-one. In PCT Application WO 91/14679 published 3 Oct. 1991, there is described a family of imidazol-4-one biphenylmethyl compounds as angiotensin II antagonists, including compounds having the 5-position of the imidazol-4-one moiety substituted with spirocyclopentyl, or diethyl, or other alkyl groups. EP #475,898 published 18 Mar. 1992 describes a class of imidazol-4-one and triazol-3-one biphenylmethyl compounds as angiotensin II antagonists, including the compound 2-(n-Butyl)-4-ethyl-5-oxo-1-[2'-(1H-tetrazol-5-yl)biphenyl-4-ylmethyl]-4,5-dihydro-1H-imidazole. In PCT Application WO 92/07834 published 14 May 1992, there is described a family of N-substituted imidazol-2-one biphenylmethyl compounds as angiotensin II antagonists, including the compound 4-butyl-1-(2-chlorophenyl)-3-[2'-(1H-tetrazol-5-yl)[1,1'-biphenyl]-4-yl]methyl-2H-imidazole-2-one.

DESCRIPTION OF THE INVENTION

A class of mono- or polysubstituted 1-phenyl-imidazol-2-one biphenylmethyl compounds useful in treating circulatory disorders, particularly cardiovascular disorders, is defined by Formula I:

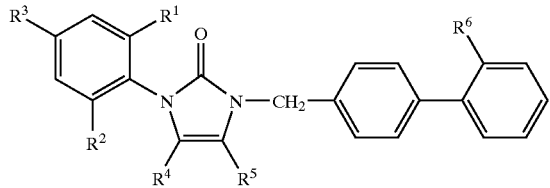

(I)

wherein each of $R^1$, $R^2$ and $R^3$ is independently selected from hydrido, alkyl, alkoxy, cyano, halo, hydroxy, nitro, amino, alkylamino, carboxyl, alkoxycarbonyl, formyl, alkylcarbonyl and haloalkylcarbonyl; with the proviso that at least one of $R^1$, $R^2$ and $R^3$ must be a substituent other than hydrido, and with the further proviso that when each of $R^1$ and $R^3$ is hydrido, then $R^2$ cannot be chloro; wherein $R^4$ is selected from hydrido, alkyl, halo, haloalkyl, formyl, carboxyl and alkoxyalkyl; wherein $R^5$ is selected from alkyl, phenyl, phenylalkyl, cycloalkyl and cycloalkylalkyl; and wherein $R^6$ is an acidic group selected from COOH and

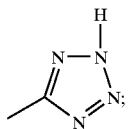

or a stereoisomer or a tautomer thereof or a pharmaceutically-acceptable salt thereof.

Regioisomers of compounds of Formula I are also embraced as part of the invention, particularly those regioisomers formed by various substitutions on nitrogen atoms of the imidazole ring relative to substitutions on the carbon atoms of the imidazole ring. For purposes of nomenclature, a numbering system for the imidazole ring is shown below for a preferred set of compounds of the invention within Formula I:

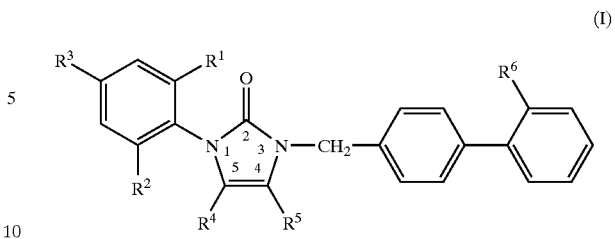

(I)

wherein each of $R^1$, $R^2$, $R^3$, $R^4$, $R^5$ and $R^6$ is defined above.

Compounds of Formula I would be useful in treating a variety of circulatory disorders and circulatory-related disorders, including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis, or to treat coronary hypertrophy arising from aortal stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

A preferred class of compounds consists of those compounds within Formula I wherein each of $R^1$, $R^2$ and $R^3$ is independently selected from hydrido, methyl, ethyl, n-propyl, isopropyl, tert-butyl, methoxy, ethoxy, propoxy, isopropoxy, tert-butoxy, cyano, fluoro, chloro, bromo, iodo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; with the proviso that at least one of $R^1$, $R^2$ and $R^3$ must be a substituent other than hydrido, and with the further proviso that when each of $R^1$ and $R^3$ is hydrido, then $R^2$ cannot be chloro; wherein $R^4$ is selected from hydrido, methyl, fluoro, chloro, monofluoromethyl, difluoromethyl, trifluoromethyl, formyl, carboxyl and dimethoxymethyl; wherein $R^5$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; and wherein $R^6$ is an acidic group selected from COOH and

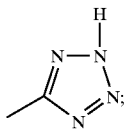

or a stereoisomer or a tautomer thereof or a pharmaceutically-acceptable salt thereof.

A first family of more preferred compounds consists of those compounds within Formula I wherein $R^1$ is selected from methyl, ethyl, n-propyl, isopropyl, tert-butyl, hydroxy, methoxy, fluoro, bromo, iodo, carboxyl, amino, cyano, formyl, methylcarbonyl and trifluoromethylcarbonyl; wherein each of $R^2$, $R^3$ and $R^4$ is hydrido; wherein $R^5$ is selected from methyl, ethyl, n-propyl, isopropyl, n-butyl, sec-butyl, isobutyl, tert-butyl and n-pentyl; and wherein $R^6$ is

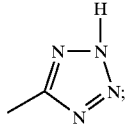

or a stereoisomer or a tautomer thereof or a pharmaceutically-acceptable salt thereof.

A group of specific compounds of particular interest within this first family of more preferred compounds of Formula I consists of mono-substituted-phenyl-type compounds, their stereoisomers and tautomers, and the pharmaceutically-acceptable salts thereof, said compounds consisting of 1-(2-methylphenyl)-4-propyl-1,3-dihydro-3-[2'-(1H-tetrazol-5-yl)[1,1'-biphenyl]-4-ylmethyl]-2H-imidazol-2-one;
1-(2-ethylphenyl)-4-propyl-1,3-dihydro-3-[2'-(1H-tetrazol-5-yl)[1,1'-biphenyl]-4-ylmethyl]-2H-imidazol-2-one;
1-(2-propylphenyl)-4-propyl-1,3-dihydro-3-[2'-(1H-tetrazol-5-yl)[1,1'-biphenyl]-4-ylmethyl]-2H-imidazol-2-one;
1-(2-isopropylphenyl)-4-propyl-1,3-dihydro-3-[2'-(1H-tetrazol-5-yl)[1,1'-biphenyl]-4-ylmethyl]-2H-imidazol-2-one;
1-(2-tertbutylphenyl)-4-propyl-1,3-dihydro-3-[2'-(1H-tetrazol-5-yl)[1,1'-biphenyl]-4-ylmethyl]-2H-imidazol-2-one;
1-(2-fluorophenyl)-4-propyl-1,3-dihydro-3-[2'-(1H-tetrazol-5-yl)[1,1'-biphenyl]-4-ylmethyl]-2H-imidazol-2-one;
1-(2-chlorophenyl)-4-propyl-1,3-dihydro-3-[2'-(1H-tetrazol-5-yl)[1,1'-biphenyl]-4-ylmethyl]-2H-imidazol-2-one;
1-(2-bromophenyl)-4-propyl-1,3-dihydro-3-[2'-(1H-tetrazol-5-yl)[1,1'-biphenyl]-4-ylmethyl]-2H-imidazol-2-one;
1-(2-iodophenyl)-4-propyl-1,3-dihydro-3-[2'-(1H-tetrazol-5-yl)[1,1'-biphenyl]-4-ylmethyl]-2H-imidazol-2-one;
1-(2-methoxyphenyl)-4-propyl-1,3-dihydro-3-[2'-(1H-tetrazol-5-yl)[1,1'-biphenyl]-4-ylmethyl]-2H-imidazol-2-one;
1-(2-hydroxyphenyl)-4-propyl-1,3-dihydro-3-[2'-(1H-tetrazol-5-yl)[1,1'-biphenyl]-4-ylmethyl]-2H-imidazol-2-one;
1-(2-cyanophenyl)-4-propyl-1,3-dihydro-3-[2'-(1H-tetrazol-5-yl)[1,1'-biphenyl]-4-ylmethyl]-2H-imidazol-2-one;
1-(2-carboxyphenyl)-4-propyl-1,3-dihydro-3-[2'-(1H-tetrazol-5-yl)[1,1'-biphenyl]-4-ylmethyl]-2H-imidazol-2-one;
1-(2-aminophenyl)-4-propyl-1,3-dihydro-3-[2'-(1H-tetrazol-5-yl)[1,1'-biphenyl]-4-ylmethyl]-2H-imidazol-2-one;
1-(2-acetylphenyl)-4-propyl-1,3-dihydro-3-[2'-(1H-tetrazol-5-yl)[1,1'-biphenyl]-4-ylmethyl]-2H-imidazol-2-one;
1-(2-trifluoroacetylphenyl)-4-propyl-1,3-dihydro-3-[2'-(1H-tetrazol-5-yl)[1,1'-biphenyl]-4-ylmethyl]-2H-imidazol-2-one;
1-(2-methylphenyl)-4-butyl-1,3-dihydro-3-[2'-(1H-tetrazol-5-yl)[1,1'-biphenyl]-4-ylmethyl]-2H-imidazol-2-one;
1-(2-ethylphenyl)-4-butyl-1,3-dihydro-3-[2'-(1H-tetrazol-5-yl)[1,1'-biphenyl]-4-ylmethyl]-2H-imidazol-2-one;
1-(2-propylphenyl)-4-butyl-1,3-dihydro-3-[2'-(1H-tetrazol-5-yl)[1,1'-biphenyl]-4-ylmethyl]-2H-imidazol-2-one;
1-(2-isopropylphenyl)-4-butyl-1,3-dihydro-3-[2'-(1H-tetrazol-5-yl)[1,1'-biphenyl]-4-ylmethyl]-2H-imidazol-2-one;
1-(2-tertbutylphenyl)-4-butyl-1,3-dihydro-3-[2'-(1H-tetrazol-5-yl)[1,1'-biphenyl]-4-ylmethyl]-2H-imidazol-2-one;
1-(2-fluorophenyl)-4-butyl-1,3-dihydro-3-[2'-(1H-tetrazol-5-yl)[1,1'-biphenyl]-4-ylmethyl]-2H-imidazol-2-one;
1-(2-chlorophenyl)-4-butyl-1,3-dihydro-3-[2'-(1H-tetrazol-5-yl)[1,1'-biphenyl]-4-ylmethyl]-2H-imidazol-2-one;
1-(2-bromophenyl)-4-butyl-1,3-dihydro-3-[2'-(1H-tetrazol-5-yl)[1,1'-biphenyl]-4-ylmethyl]-2H-imidazol-2-one;
1-(2-iodophenyl)-4-butyl-1,3-dihydro-3-[2'-(1H-tetrazol-5-yl)[1,1'-biphenyl]-4-ylmethyl]-2H-imidazol-2-one;
1-(2-methoxyphenyl)-4-butyl-1,3-dihydro-3-[2'-(1H-tetrazol-5-yl)[1,1'-biphenyl]-4-ylmethyl]-2H-imidazol-2-one;
1-(2-hydroxyphenyl)-4-butyl-1,3-dihydro-3-[2'-(1H-tetrazol-5-yl)[1,1'-biphenyl]-4-ylmethyl]-2H-imidazol-2-one;
1-(2-cyanophenyl)-4-butyl-1,3-dihydro-3-[2'-(1H-tetrazol-5-yl)[1,1'-biphenyl]-4-ylmethyl]-2H-imidazol-2-one;
1-(2-carboxyphenyl)-4-butyl-1,3-dihydro-3-[2'-(1H-tetrazol-5-yl)[1,1'-biphenyl]-4-ylmethyl]-2H-imidazol-2-one;
1-(2-aminophenyl)-4-butyl-1,3-dihydro-3-[2'-(1H-tetrazol-5-yl)[1,1'-biphenyl]-4-ylmethyl]-2H-imidazol-2-one;
1-(2-acetylphenyl)-4-butyl-1,3-dihydro-3-[2'-(1H-tetrazol-5-yl)[1,1'-biphenyl]-4-ylmethyl]-2H-imidazol-2-one;
1-(2-trifluoroacetylphenyl)-4-butyl-1,3-dihydro-3-[2'-(1H-tetrazol-5-yl)[1,1'-biphenyl]-4-ylmethyl]-2H-imidazol-2-one;
1-(2-methylphenyl)-4-pentyl-1,3-dihydro-3-[2'-(1H-tetrazol-5-yl)[1,1'-biphenyl]-4-ylmethyl]-2H-imidazol-2-one;
1-(2-ethylphenyl)-4-pentyl-1,3-dihydro-3-[2'-(1H-tetrazol-5-yl)[1,1'-biphenyl]-4-ylmethyl]-2H-imidazol-2-one;
1-(2-propylphenyl)-4-pentyl-1,3-dihydro-3-[2'-(1H-tetrazol-5-yl)[1,1'-biphenyl]-4-ylmethyl]-2H-imidazol-2-one;
1-(2-isopropylphenyl)-4-pentyl-1,3-dihydro-3-[2'-(1H-tetrazol-5-yl)[1,1'-biphenyl]-4-ylmethyl]-2H-imidazol-2-one;
1-(2-tertbutylphenyl)-4-pentyl-1,3-dihydro-3-[2'-(1H-tetrazol-5-yl)[1,1'-biphenyl]-4-ylmethyl]-2H-imidazol-2-one;
1-(2-fluorophenyl)-4-pentyl-1,3-dihydro-3-[2'-(1H-tetrazol-5-yl)[1,1'-biphenyl]-4-ylmethyl]-2H-imidazol-2-one;
1-(2-chlorophenyl)-4-pentyl-1,3-dihydro-3-[2'-(1H-tetrazol-5-yl)[1,1'-biphenyl]-4-ylmethyl]-2H-imidazol-2-one;
1-(2-bromophenyl)-4-pentyl-1,3-dihydro-3-[2'-(1H-tetrazol-5-yl)[1,1'-biphenyl]-4-ylmethyl]-2H-imidazol-2-one;
1-(2-iodophenyl)-4-pentyl-1,3-dihydro-3-[2'-(1H-tetrazol-5-yl)[1,1'-biphenyl]-4-ylmethyl]-2H-imidazol-2-one;
1-(2-methoxyphenyl)-4-pentyl-1,3-dihydro-3-[2'-(1H-tetrazol-5-yl)[1,1'-biphenyl]-4-ylmethyl]-2H-imidazol-2-one;
1-(2-hydroxyphenyl)-4-pentyl-1,3-dihydro-3-[2'-(1H-tetrazol-5-yl)[1,1'-biphenyl]-4-ylmethyl]-2H-imidazol-2-one;
1-(2-cyanophenyl)-4-pentyl-1,3-dihydro-3-[2'-(1H-tetrazol-5-yl)[1,1'-biphenyl]-4-ylmethyl]-2H-imidazol-2-one;
1-(2-carboxyphenyl)-4-pentyl-1,3-dihydro-3-[2'-(1H-tetrazol-5-yl)[1,1'-biphenyl]-4-ylmethyl]-2H-imidazol-2-one;

1-(2-aminophenyl)-4-pentyl-1,3-dihydro-3-[2'-(1H-tetrazol-5-yl)[1,1'-biphenyl]-4-ylmethyl]-2H-imidazol-2-one;
1-(2-acetylphenyl)-4-pentyl-1,3-dihydro-3-[2'-(1H-tetrazol-5-yl)[1,1'-biphenyl]-4-ylmethyl]-2H-imidazol-2-one; and
1-(2-trifluoroacetylphenyl)-4-pentyl-1,3-dihydro-3-[2'-(1H-tetrazol-5-yl)[1,1'-biphenyl]-4-ylmethyl]-2H-imidazol-2-one.

A group of specific compounds of particular interest within this first family of more preferred compounds of Formula I consists of mono-substituted-phenyl-type compounds, their stereoisomers and tautomers, and the pharmaceutically-acceptable salts thereof, said compounds consisting of 1-(2-methylphenyl)-4-butyl-1,3-dihydro-3-[2'-(1H-tetrazol-5-yl)[1,1'-biphenyl]-4-ylmethyl]-2H-imidazol-2-one;
1-(2-ethylphenyl)-4-butyl-1,3-dihydro-3-[2'-(1H-tetrazol-5-yl)[1,1'-biphenyl]-4-ylmethyl]-2H-imidazol-2-one;
1-(2-propylphenyl)-4-butyl-1,3-dihydro-3-[2'-(1H-tetrazol-5-yl)[1,1'-biphenyl]-4-ylmethyl]-2H-imidazol-2-one;
1-(2-isopropylphenyl)-4-butyl-1,3-dihydro-3-[2'-(1H-tetrazol-5-yl)[1,1'-biphenyl]-4-ylmethyl]-2H-imidazol-2-one;
1-(2-tertbutylphenyl)-4-butyl-1,3-dihydro-3-[2'-(1H-tetrazol-5-yl)[1,1'-biphenyl]-4-ylmethyl]-2H-imidazol-2-one;
1-(2-fluorophenyl)-4-butyl-1,3-dihydro-3-[2'-(1H-tetrazol-5-yl)[1,1'-biphenyl]-4-ylmethyl]-2H-imidazol-2-one;
1-(2-chlorophenyl)-4-butyl-1,3-dihydro-3-[2'-(1H-tetrazol-5-yl)[1,1'-biphenyl]-4-ylmethyl]-2H-imidazol-2-one;
1-(2-bromophenyl)-4-butyl-1,3-dihydro-3-[2'-(1H-tetrazol-5-yl)[1,1'-biphenyl]-4-ylmethyl]-2H-imidazol-2-one;
1-(2-iodophenyl)-4-butyl-1,3-dihydro-3-[2'-(1H-tetrazol-5-yl)[1,1'-biphenyl]-4-ylmethyl]-2H-imidazol-2-one;
1-(2-methoxyphenyl)-4-butyl-1,3-dihydro-3-[2'-(1H-tetrazol-5-yl)[1,1'-biphenyl]-4-ylmethyl]-2H-imidazol-2-one;
1-(2-hydroxyphenyl)-4-butyl-1,3-dihydro-3-[2'-(1H-tetrazol-5-yl)[1,1'-biphenyl]-4-ylmethyl]-2H-imidazol-2-one;
1-(2-cyanophenyl)-4-butyl-1,3-dihydro-3-[2'-(1H-tetrazol-5-yl)[1,1'-biphenyl]-4-ylmethyl]-2H-imidazol-2-one;
1-(2-carboxyphenyl)-4-butyl-1,3-dihydro-3-[2'-(1H-tetrazol-5-yl)[1,1'-biphenyl]-4-ylmethyl]-2H-imidazol-2-one;
1-(2-aminophenyl)-4-butyl-1,3-dihydro-3-[2'-(1H-tetrazol-5-yl)[1,1'-biphenyl]-4-ylmethyl]-2H-imidazol-2-one.
1-(2-acetylphenyl)-4-butyl-1,3-dihydro-3-[2'-(1H-tetrazol-5-yl)[1,1'-biphenyl]-4-ylmethyl]-2H-imidazol-2-one; and
1-(2-trifluoroacetylphenyl)-4-butyl-1,3-dihydro-3-[2'-(1H-tetrazol-5-yl)[1,1'-biphenyl]-4-ylmethyl]-2H-imidazol-2-one.

A second family of more preferred compounds consists of those compounds within Formula I wherein each of $R^1$, $R^2$ and $R^3$ is independently selected from methyl, ethyl, n-propyl, isopropyl, tert-butyl, hydroxy, methoxy, fluoro, chloro, bromo, iodo, carboxyl, amino, cyano, formyl, methylcarbonyl and trifluoromethylcarbonyl; wherein $R^3$ may further be hydrido; wherein $R^4$ is hydrido; wherein $R^5$ is selected from methyl, ethyl, n-propyl, isopropyl, n-butyl, sec-butyl, isobutyl, tert-butyl and n-pentyl; and wherein $R^6$ is

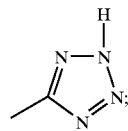

or a stereoisomer or a tautomer thereof or a pharmaceutically-acceptable salt thereof.

A group of specific compounds of particular interest within this second family of more preferred compounds of Formula I consists of poly-substituted-phenyl-type compounds, their stereoisomers and tautomers, and the pharmaceutically-acceptable salts thereof, said compounds consisting of 1-(2,6-dimethylphenyl)-4-propyl-1,3-dihydro-3-[2'-(1H-tetrazol-5-yl)[1,1'-biphenyl]-4-ylmethyl]-2H-imidazol-2-one;
1-(2-ethyl-6-methylphenyl)-4-propyl-1,3-dihydro-3-[2'-(1H-tetrazol-5-yl)[1,1'-biphenyl]-4-ylmethyl]-2H-imidazol-2-one;
1-(2-propyl-6-methylphenyl)-4-propyl-1,3-dihydro-3-[2'-(1H-tetrazol-5-yl)[1,1'-biphenyl]-4-ylmethyl]-2H-imidazol-2-one;
1-(2-isopropyl-6-methylphenyl)-4-propyl-1,3-dihydro-3-[2'-(1H-tetrazol-5-yl)[1,1'-biphenyl]-4-ylmethyl]-2H-imidazol-2-one;
1-(2-tertbutyl-6-methylphenyl)-4-propyl-1,3-dihydro-3-[2'-(1H-tetrazol-5-yl)[1,1'-biphenyl]-4-ylmethyl]-2H-imidazol-2-one;
1-(2-fluoro-6-methylphenyl)-4-propyl-1,3-dihydro-3-[2'-(1H-tetrazol-5-yl)[1,1'-biphenyl]-4-ylmethyl]-2H-imidazol-2-one;
1-(2-chloro-6-methylphenyl)-4-propyl-1,3-dihydro-3-[2'-(1H-tetrazol-5-yl)[1,1'-biphenyl]-4-ylmethyl]-2H-imidazol-2-one;
1-(2-bromo-6-methylphenyl)-4-propyl-1,3-dihydro-3-[2'-(1H-tetrazol-5-yl)[1,1'-biphenyl]-4-ylmethyl]-2H-imidazol-2-one;
1-(2-methoxy-6-methylphenyl)-4-propyl-1,3-dihydro-3-[2'-(1H-tetrazol-5-yl)[1,1'-biphenyl]-4-ylmethyl]-2H-imidazol-2-one;
1-(2-carboxy-6-methylphenyl)-4-propyl-1,3-dihydro-3-[2'-(1H-tetrazol-5-yl)[1,1'-biphenyl]-4-ylmethyl]-2H-imidazol-2-one;
1-(2-acetyl-6-methylphenyl)-4-propyl-1,3-dihydro-3-[2'-(1H-tetrazol-5-yl)[1,1'-biphenyl]-4-ylmethyl]-2H-imidazol-2-one;
1-(2,6-diethylphenyl)-4-propyl-1,3-dihydro-3-[2'-(1H-tetrazol-5-yl)[1,1'-biphenyl]-4-ylmethyl]-2H-imidazol-2-one;
1-(2-propyl-6-ethylphenyl)-4-propyl-1,3-dihydro-3-[2'-(1H-tetrazol-5-yl)[1,1'-biphenyl]-4-ylmethyl]-2H-imidazol-2-one;
1-(2-isopropyl-6-ethylphenyl)-4-propyl-1,3-dihydro-3-[2'-(1H-tetrazol-5-yl)[1,1'-biphenyl]-4-ylmethyl]-2H-imidazol-2-one;
1-(2-tertbutyl-6-ethylphenyl)-4-propyl-1,3-dihydro-3-[2'-(1H-tetrazol-5-yl)[1,1'-biphenyl]-4-ylmethyl]-2H-imidazol-2-one;
1-(2-fluoro-6-ethylphenyl)-4-propyl-1,3-dihydro-3-[2'-(1H-tetrazol-5-yl)[1,1'-biphenyl]-4-ylmethyl]-2H-imidazol-2-one;
1-(2-chloro-6-ethylphenyl)-4-propyl-1,3-dihydro-3-[2'-(1H-tetrazol-5-yl)[1,1'-biphenyl]-4-ylmethyl]-2H-imidazol-2-one;
1-(2-bromo-6-ethylphenyl)-4-propyl-1,3-dihydro-3-[2'-(1H-tetrazol-5-yl)[1,1'-biphenyl]-4-ylmethyl]-2H-imidazol-2-one;

1-(2-methoxy-6-ethylphenyl)-4-propyl-1,3-dihydro-3-[2'-(1H-tetrazol-5-yl)[1,1'-biphenyl]-4-ylmethyl]-2H-imidazol-2-one;

1-(2-carboxy-6-ethylphenyl)-4-propyl-1,3-dihydro-3-[2'-(1H-tetrazol-5-yl)[1,1'-biphenyl]-4-ylmethyl]-2H-imidazol-2-one;

1-(2-acetyl-6-ethylphenyl)-4-propyl-1,3-dihydro-3-[2'-(1H-tetrazol-5-yl)[1,1'-biphenyl]-4-ylmethyl]-2H-imidazol-2-one;

1-(2-methyl-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-ethyl-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-propyl-6-isopropylphenyl)-4-propyl-1,3-dihydro-3-[2'-(1H-tetrazol-5-yl)[1,1'-biphenyl]-4-ylmethyl]-2H-imidazol-2-one;

1-(2,6-diisopropylphenyl)-4-propyl-1,3-dihydro-3-[2'-(1H-tetrazol-5-yl)[1,1'-biphenyl]-4-ylmethyl]-2H-imidazol-2-one;

1-(2-tertbutyl-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-fluoro-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-chloro-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-bromo-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-methoxy-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-carboxy-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-acetyl-6-isopropylphenyl)-4-propyl-1,3-dihydro-3-[2'-(1H-tetrazol-5-yl)[1,1'-biphenyl]-4-ylmethyl]-2H-imidazol-2-one;

1-(2-methyl-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-ethyl-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-propyl-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-isopropyl-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2,6-ditertbutylphenyl)-4-propyl-1,3-dihydro-3-[2'-(1H-tetrazol-5-yl)[1,1'-biphenyl]-4-ylmethyl]-2H-imidazol-2-one;

1-(2-fluoro-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-chloro-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-bromo-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-methoxy-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-carboxy-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-acetyl-6-tertbutylphenyl)-4-propyl-1,3-dihydro-3-[2'-(1H-tetrazol-5-yl)[1,1'-biphenyl]-4-ylmethyl]-2H-imidazol-2-one;

1-(2-methyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2-ethyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2-propyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2-isopropyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2-tertbutyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2,6-difluorophenyl)-4-propyl-1,3-dihydro-3-[2'-(1H-tetrazol-5-yl)[1,1'-biphenyl]-4-ylmethyl]-2H-imidazol-2-one;

1-(2-chloro-6-fluorophenyl)-4-propyl-1,3-dihydro-3-[2'-(1H-tetrazol-5-yl)[1,1'-biphenyl]-4-ylmethyl]-2H-imidazol-2-one;

1-(2-bromo-6-fluorophenyl)-4-propyl-1,3-dihydro-3-[2'-(1H-tetrazol-5-yl)[1,1'-biphenyl]-4-ylmethyl]-2H-imidazol-2-one;

1-(2-methoxy-6-fluorophenyl)-4-propyl-1,3-dihydro-3-[2'-(1H-tetrazol-5-yl)[1,1'-biphenyl]-4-ylmethyl]-2H-imidazol-2-one;

1-(2-carboxy-6-fluorophenyl)-4-propyl-1,3-dihydro-3-[2'-(1H-tetrazol-5-yl)[1,1'-biphenyl]-4-ylmethyl]-2H-imidazol-2-one;

1-(2-acetyl-6-fluorophenyl)-4-propyl-1,3-dihydro-3-[2'-(1H-tetrazol-5-yl)[1,1'-biphenyl]-4-ylmethyl]-2H-imidazol-2-one;

1-(2-methyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-ethyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-propyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-isopropyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-tertbutyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-fluoro-6-chlorophenyl)-4-propyl-1,3-dihydro-3-[2'-(1H-tetrazol-5-yl)[1,1'-biphenyl]-4-ylmethyl]-2H-imidazol-2-one;

1-(2,6-dichlorophenyl)-4-propyl-1,3-dihydro-3-[2'-(1H-tetrazol-5-yl)[1,1'-biphenyl]-4-ylmethyl]-2H-imidazol-2-one;

1-(2-bromo-6-chlorophenyl)-4-propyl-1,3-dihydro-3-[2'-(1H-tetrazol-5-yl)[1,1'-biphenyl]-4-ylmethyl]-2H-imidazol-2-one;

1-(2-methoxy-6-chlorophenyl)-4-propyl-1,3-dihydro-3-[2'-(1H-tetrazol-5-yl)[1,1'-biphenyl]-4-ylmethyl]-2H-imidazol-2-one;

1-(2-carboxy-6-chlorophenyl)-4-propyl-1,3-dihydro-3-[2'-(1H-tetrazol-5-yl)[1,1'-biphenyl]-4-ylmethyl]-2H-imidazol-2-one;

1-(2-acetyl-6-chlorophenyl)-4-propyl-1,3-dihydro-3-[2'-(1H-tetrazol-5-yl)[1,1'-biphenyl]-4-ylmethyl]-2H-imidazol-2-one;

1-(2-methyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-ethyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-propyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-isopropyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-tertbutyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-fluoro-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-chloro-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-bromo-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-methoxy-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-carboxy-6-methoxyphenyl)-4-propyl-1,3-dihydro-3-[2'-(1H-tetrazol-5-yl)[1,1'-biphenyl]-4-ylmethyl]-2H-imidazol-2-one;

1-(2-acetyl-6-methoxyphenyl)-4-propyl-1,3-dihydro-3-[2'-(1H-tetrazol-5-yl)[1,1'-biphenyl]-4-ylmethyl]-2H-imidazol-2-one;

1-(2,6-dimethylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-methylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-methylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-methylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-methylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2,6-diethylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-ethylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-ethylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-ethylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-ethylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-ethylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2,6-diisopropylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2,6-ditertbutylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-ethyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-propyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2,6-difluorophenyl)-4-butyl-1,3-dihydro-3-[2'-(1H-tetrazol-5-yl)[1,1'-biphenyl]-4-ylmethyl]-2H-imidazol-2-one;

1-(2-chloro-6-fluorophenyl)-4-butyl-1,3-dihydro-3-[2'-(1H-tetrazol-5-yl)[1,1'-biphenyl]-4-ylmethyl]-2H-imidazol-2-one;

1-(2-bromo-6-fluorophenyl)-4-butyl-1,3-dihydro-3-[2'-(1H-tetrazol-5-yl)[1,1'-biphenyl]-4-ylmethyl]-2H-imidazol-2-one;

1-(2-methoxy-6-fluorophenyl)-4-butyl-1,3-dihydro-3-[2'-(1H-tetrazol-5-yl)[1,1'-biphenyl]-4-ylmethyl]-2H-imidazol-2-one;

1-(2-carboxy-6-fluorophenyl)-4-butyl-1,3-dihydro-3-[2'-(1H-tetrazol-5-yl)[1,1'-biphenyl]-4-ylmethyl]-2H-imidazol-2-one;

1-(2-acetyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-methyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-ethyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-propyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-fluoro-6-chlorophenyl)-4-butyl-1,3-dihydro-3-[2'-(1H-tetrazol-5-yl)[1,1'-biphenyl]-4-ylmethyl]-2H-imidazol-2-one;

1-(2,6-dichlorophenyl)-4-butyl-1,3-dihydro-3-[2'-(1H-tetrazol-5-yl)[1,1'-biphenyl]-4-ylmethyl]-2H-imidazol-2-one;

1-(2-bromo-6-chlorophenyl)-4-butyl-1,3-dihydro-3-[2'-(1H-tetrazol-5-yl)[1,1'-biphenyl]-4-ylmethyl]-2H-imidazol-2-one;

1-(2-methoxy-6-chlorophenyl)-4-butyl-1,3-dihydro-3-[2'-(1H-tetrazol-5-yl)[1,1'-biphenyl]-4-ylmethyl]-2H-imidazol-2-one;

1-(2-carboxy-6-chlorophenyl)-4-butyl-1,3-dihydro-3-[2'-(1H-tetrazol-5-yl)[1,1'-biphenyl]-4-ylmethyl]-2H-imidazol-2-one;

1-(2-acetyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-methyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-propyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-bromo-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2,6-dimethylphenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-methylphenyl)-4-pentyl-1,3-dihydro-3-[2'-(1H-tetrazol-5-yl)[1,1'-biphenyl]-4-ylmethyl]-2H-imidazol-2-one;

1-(2-propyl-6-methylphenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-methylphenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-methylphenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-methylphenyl)-4-pentyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-pentyl-1,3-dihydro-3-[2'-(1H-tetrazol-5-yl)[1,1'-biphenyl]-4-ylmethyl]-2H-imidazol-2-one;

1-(2-bromo-6-methylphenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-methylphenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-methylphenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-methylphenyl)-4-pentyl-1,3-dihydro-3-[2'-(1H-tetrazol-5-yl)[1,1'-biphenyl]-4-ylmethyl]-2H-imidazol-2-one;

1-(2-methyl-6-ethylphenyl)-4-pentyl-1,3-dihydro-3-[2'-(1H-tetrazol-5-yl)[1,1'-biphenyl]-4-ylmethyl]-2H-imidazol-2-one;

1-(2,6-diethylphenyl)-4-pentyl-1,3-dihydro-3-[2'-(1H-tetrazol-5-yl)[1,1'-biphenyl]-4-ylmethyl]-2H-imidazol-2-one;

1-(2-propyl-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-chloro-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-bromo-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-ethylphenyl)-4-pentyl-1,3-dihydro-3-[2'-(1H-tetrazol-5-yl)[1,1'-biphenyl]-4-ylmethyl]-2H-imidazol-2-one;

1-(2-methyl-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-propyl-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2,6-diisopropylphenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-chloro-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-bromo-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-isopropylphenyl)-4-pentyl-1,3-dihydro-3-[2'-(1H-tetrazol-5-yl)[1,1'-biphenyl]-4-ylmethyl]-2H-imidazol-2-one;

1-(2-methyl-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-propyl-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2,6-ditertbutylphenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-chloro-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-bromo-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-tertbutylphenyl)-4-pentyl-1,3-dihydro-3-[2'-(1H-tetrazol-5-yl)[1,1'-biphenyl]-4-ylmethyl]-2H-imidazol-2-one;

1-(2-methyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-propyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2,6-difluorophenyl)-4-pentyl-1,3-dihydro-3-[2'-(1H-tetrazol-5-yl)[1,1'-biphenyl]-4-ylmethyl]-2H-imidazol-2-one;

1-(2-chloro-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-bromo-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-fluorophenyl)-4-pentyl-1,3-dihydro-3-[2'-(1H-tetrazol-5-yl)[1,1'-biphenyl]-4-ylmethyl]-2H-imidazol-2-one;

1-(2-methyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-propyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-chlorophenyl)-4-pentyl-1,3-dihydro-3-[2'-(1H-tetrazol-5-yl)[1,1'-biphenyl]-4-ylmethyl]-2H-imidazol-2-one;

1-(2,6-dichlorophenyl)-4-pentyl-1,3-dihydro-3-[2'-(1H-tetrazol-5-yl)[1,1'-biphenyl]-4-ylmethyl]-2H-imidazol-2-one;

1-(2-bromo-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-acetyl-6-chlorophenyl)-4-pentyl-1,3-dihydro-3-[2'-(1H-tetrazol-5-yl)[1,1'-biphenyl]-4-ylmethyl]-2H-imidazol-2-one;

1-(2-methyl-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-ethyl-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-propyl-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-isopropyl-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-tertbutyl-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-fluoro-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-chloro-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-bromo-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-methoxy-6-methoxyphenyl)-4-pentyl-1,3-dihydro-3-[2'-(1H-tetrazol-5-yl)[1,1'-biphenyl]-4-ylmethyl]-2H-imidazol-2-one;

1-(2-carboxy-6-methoxyphenyl)-4-pentyl-1,3-dihydro-3-[2'-(1H-tetrazol-5-yl)[1,1'-biphenyl]-4-ylmethyl]-2H-imidazol-2-one; and 1-(2-acetyl-6-methoxyphenyl)-4-pentyl-1,3-dihydro-3-[2'-(1H-tetrazol-5-yl)[1,1'-biphenyl]-4-ylmethyl]-2H-imidazol-2-one.

A group of specific compounds of more particular interest within this second family of more preferred compounds of Formula I consists of poly-substituted-phenyl-type compounds, their stereoisomers and tautomers, and the pharmaceutically-acceptable salts thereof, said compounds consisting of 1-(2,6-dimethylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-methylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-methylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-methylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-methylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-methylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2,6-diethylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-ethylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-ethylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-ethylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-ethylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-ethylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-ethylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2,6-diisopropylphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-isopropylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-propyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2,6-ditertbutylphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-chloro-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-bromo-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-acetyl-6-tertbutylphenyl)-4-butyl-1,3-dihydro-3-[2'-(1H-tetrazol-5-yl)[1,1'-biphenyl]-4-ylmethyl]-2H-imidazol-2-one;

1-(2-methyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-ethyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-propyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2,6-difluorophenyl)-4-butyl-1,3-dihydro-3-[2'-(1H-tetrazol-5-yl)[1,1'-biphenyl]-4-ylmethyl]-2H-imidazol-2-one;

1-(2-chloro-6-fluorophenyl)-4-butyl-1,3-dihydro-3-[2'-(1H-tetrazol-5-yl)[1,1'-biphenyl]-4-ylmethyl]-2H-imidazol-2-one;

1-(2-bromo-6-fluorophenyl)-4-butyl-1,3-dihydro-3-[2'-(1H-tetrazol-5-yl)[1,1'-biphenyl]-4-ylmethyl]-2H-imidazol-2-one;

1-(2-methoxy-6-fluorophenyl)-4-butyl-1,3-dihydro-3-[2'-(1H-tetrazol-5-yl)[1,1'-biphenyl]-4-ylmethyl]-2H-imidazol-2-one;

1-(2-carboxy-6-fluorophenyl)-4-butyl-1,3-dihydro-3-[2'-(1H-tetrazol-5-yl)[1,1'-biphenyl]-4-ylmethyl]-2H-imidazol-2-one;

1-(2-acetyl-6-fluorophenyl)-4-butyl-1,3-dihydro-3-[2'-(1H-tetrazol-5-yl)[1,1'-biphenyl]-4-ylmethyl]-2H-imidazol-2-one;

1-(2-methyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-ethyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-propyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-fluoro-6-chlorophenyl)-4-butyl-1,3-dihydro-3-[2'-(1H-tetrazol-5-yl)[1,1'-biphenyl]-4-ylmethyl]-2H-imidazol-2-one;

1-(2,6-dichlorophenyl)-4-butyl-1,3-dihydro-3-[2'-(1H-tetrazol-5-yl)[1,1'-biphenyl]-4-ylmethyl]-2H-imidazol-2-one;

1-(2-bromo-6-chlorophenyl)-4-butyl-1,3-dihydro-3-[2'-(1H-tetrazol-5-yl)[1,1'-biphenyl]-4-ylmethyl]-2H-imidazol-2-one;

1-(2-methoxy-6-chlorophenyl)-4-butyl-1,3-dihydro-3-[2'-(1H-tetrazol-5-yl)[1,1'-biphenyl]-4-ylmethyl]-2H-imidazol-2-one;

1-(2-carboxy-6-chlorophenyl)-4-butyl-1,3-dihydro-3-[2'-(1H-tetrazol-5-yl)[1,1'-biphenyl]-4-ylmethyl]-2H-imidazol-2-one;

1-(2-acetyl-6-chlorophenyl)-4-butyl-1,3-dihydro-3-[2'-(1H-tetrazol-5-yl)[1,1'-biphenyl]-4-ylmethyl]-2H-imidazol-2-one;

1-(2-methyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-ethyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-propyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-isopropyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-tertbutyl-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-fluoro-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-bromo-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-methoxy-6-methoxyphenyl)-4-butyl-1,3-dihydro-3-[2'-(1H-tetrazol-5-yl)[1,1'-biphenyl]-4-ylmethyl]-2H-imidazol-2-one;

1-(2-carboxy-6-methoxyphenyl)-4-butyl-1,3-dihydro-3-[2'-(1H-tetrazol-5-yl)[1,1'-biphenyl]-4-ylmethyl]-2H-imidazol-2-one; and 1-(2-acetyl-6-methoxyphenyl)-4-butyl-1,3-dihydro-3-[2'-(1H-tetrazol-5-yl)[1,1'-biphenyl]-4-ylmethyl]-2H-imidazol-2-one.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —CH$_2$— group. Where the term "alkyl" is used, either alone or within other terms such as "haloalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The term "alkoxyl" embraces linear or branched oxy-containing radicals having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The terms "alkylcarbonyl" and "acyl" are interchangeable. An example of "alkylcarbonyl" is "acetyl". The terms "benzyl" and "phenylmethyl" are interchangeable. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

Compounds embraced by Formula I may be prepared in accordance with Schemes I-VIII, which follow, wherein the R substituents are as defined for Formula I, above, except where further noted.

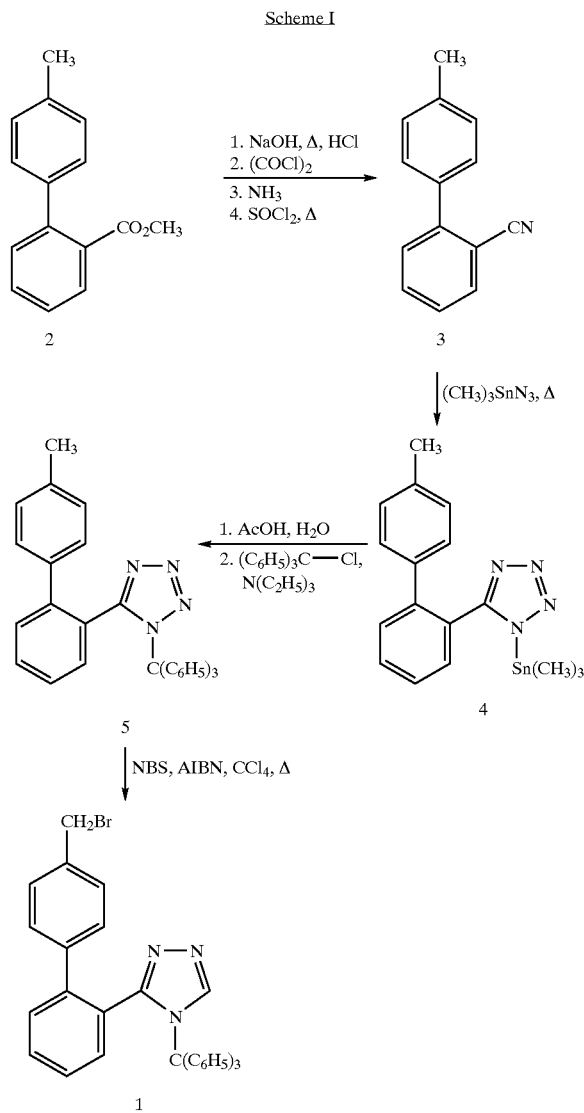

Synthetic Scheme I shows the preparation of the alkylating agent 1 where $R^5$ equal $CN_4C(C_6H_5)_3$ from the corresponding methyl ester 2 ($R^5=CO_2CH_3$). In step 1, the methyl ester is converted to the corresponding acid ($R^5=CO_2H$) by the action of sodium hydroxide/hydrochloric acid. In step 2, the acid is converted to the corresponding acid chloride ($R^5=COCl$) by the action of oxalyl chloride. In step 3, the acid chloride is converted to the corresponding primary amide ($R^5=CONH_2$) by the action of ammonia. In step 4, the amide is converted to the corresponding nitrile 3 by the action of thionyl chloride at reflux. In step 5, the nitrile 3 is reacted with trimethyltinazide in xylene at reflux to give the corresponding trimethytin protected tetrazole 4. In step 5, 6, and 7 deprotection with acetic acid/water and reprotection with triphenylmethyl chloride/triethylamine gives the N-trityltetrazole 5 ($R^5=CN_4C(C_6H_5)_3$). In step 8, bromination with N-bromosuccinimide (NBS) provides the N-trityltetrazole alkylating agent 1.

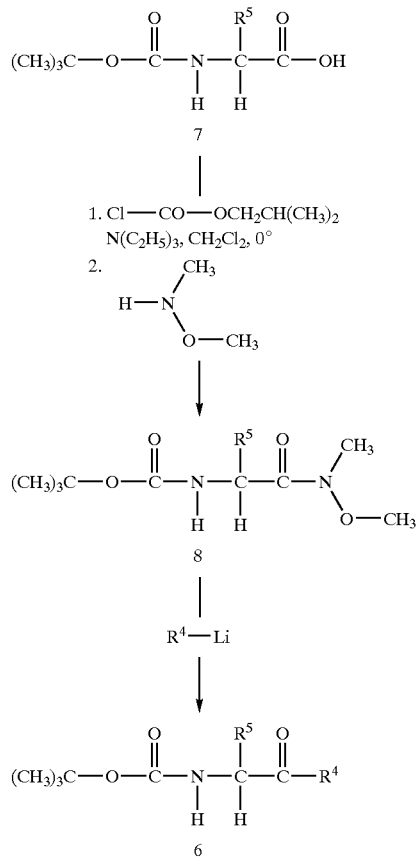

Synthetic Scheme II shows the preparation of N-Boc-amino ketones 6 (or aldehydes when $R^4=H$) from the corresponding N-Boc-amino acides 7. In step 1, the amino acid 7 is reacted with isobutyl chloroformate in the presence of triethylamine and subsequently with N,O-dimethylhydroxylamine to give the corresponding N-methoxy-N-methylamide 8. In step 2, the amide 8 is reacted with an organolithium reagent $R^4$—Li (or lithium aluminum hydride (LAH) when $R^4H$) to give the desired ketone 6 (or aldehyde when $R^4=H$).

Scheme III

METHOD A:

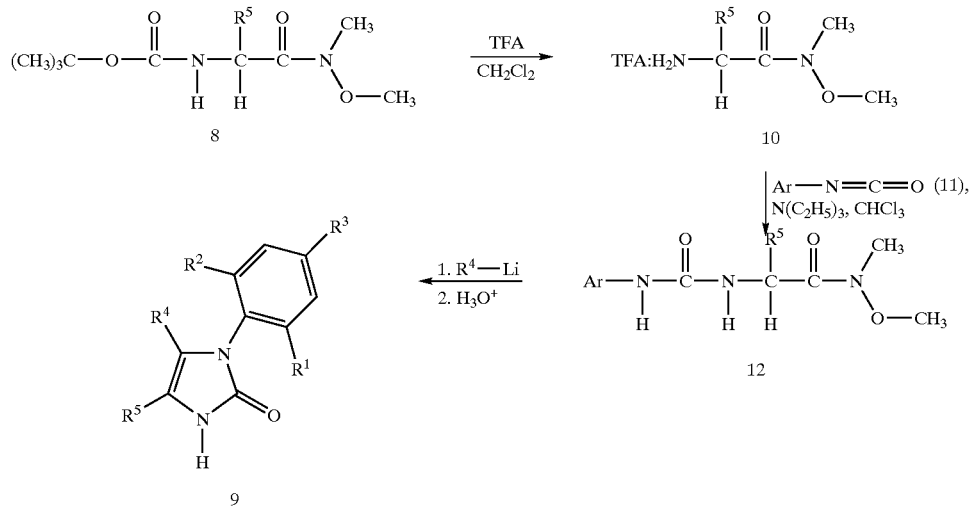

Synthetic Scheme III shows the preparation of imidazol-2-ones 9 from the corresponding amides 8 via Method A. In step 1, the protected amide 8 (prepared in Scheme II) is reacted with trifluoroacetic acid (TFA) to give the TFA salt 10 of the free amine. In step 2, the salt 10 is reacted with the appropriate isocyanate 11 in the presence of triethylamine to give the urea 12. In step 3, the urea 12 is reacted with an organolithium reagent $R^4$—Li (or lithium aluminum hydride (LAH) when $R^4$=H) and subsequently cyclized to the imidazole-2-one 9 on treatment with dilute acid during the work-up procedure.

Scheme IV

METHOD B:

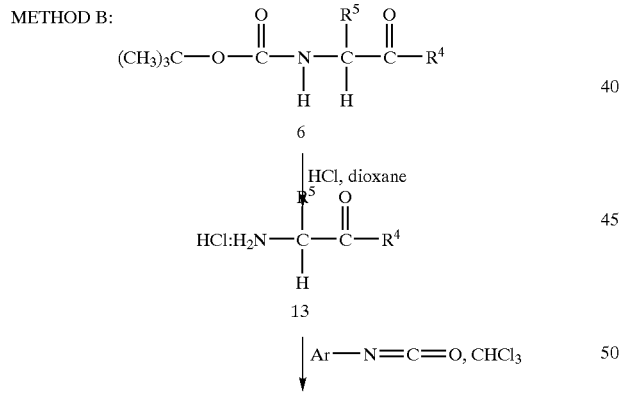

-continued

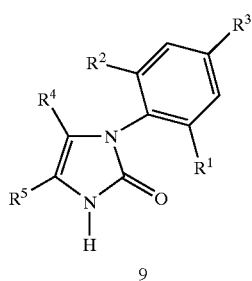

Synthetic Scheme IV shows the preparation of imidazol-2-ones 9 from the corresponding N-Boc-protected amino ketones 6 (or aldehydes when $R^4$=H) via Method B. In step 1, the carbonyl compound 6 (prepared in Scheme II) is reacted with anhydrous hydrogen chloride in dioxane to give the HCl salt 13. In step 2, the salt 13 is reacted with the appropriate isocyanate 11 in chloroform to give the imidazol-2-one 9 directly.

Scheme V

METHOD C:

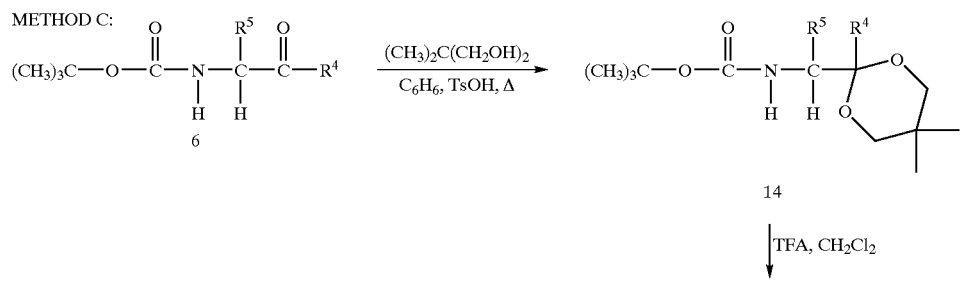

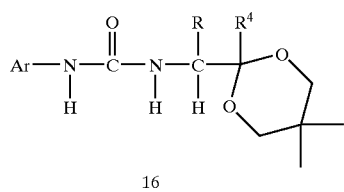

16

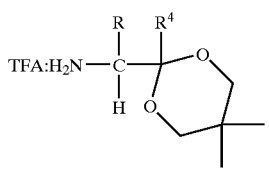

15

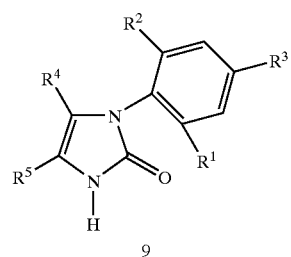

9

Synthetic Scheme V shows the preparation of imidazol-2-ones 9 from the corresponding N-Boc-protected amino ketones 6 (or aldehydes when $R^4$=H) via Method C. In step 1, the carbonyl compound 6 (prepared in Scheme II) is reacted with 2,2-dimethyl-1,3-propandiol to give the cyclic ketal 14. In step 2, the ketal 14 is reacted with TFA to give the TFA salt 15 of the free amine. In step 3, the salt 15 is reacted with the appropriate isocyanate 11 in the presence of triethylamine to give the urea ketal 16. In step 4, the urea ketal 16 is reacted with 6N hydrochloric acid at 60° C. to give the desired imidazol-2-one 9 directly.

Scheme VI

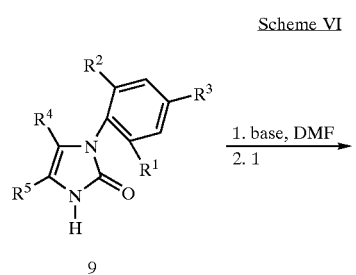

9

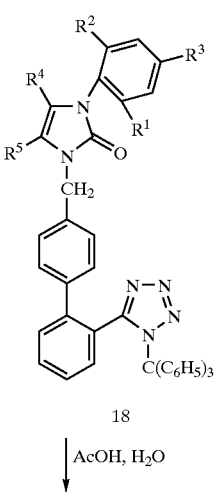

18

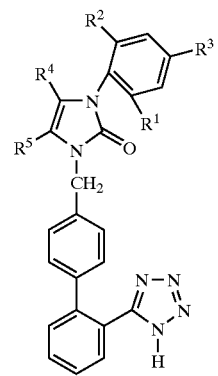

17

Synthetic Scheme VI shows the preparation of biphenylmethylimidazol-2-ones 17 from the parent imidazol-2-ones 9 (prepared in Scheme III, Scheme IV, or Scheme V). In step 1, the imidazol-2-one 9 is first treated with a base, such as potassium t-butoxide, and subsequently with the alkylating agent 1 (prepared in Scheme I) to give the protected coupled imidazol-2-one 18. In step 2, the N-trityl (triphemylmethyl) protected 18 is deprotected with acetic acid/water to give the desired angiotensin II antagonist 17.

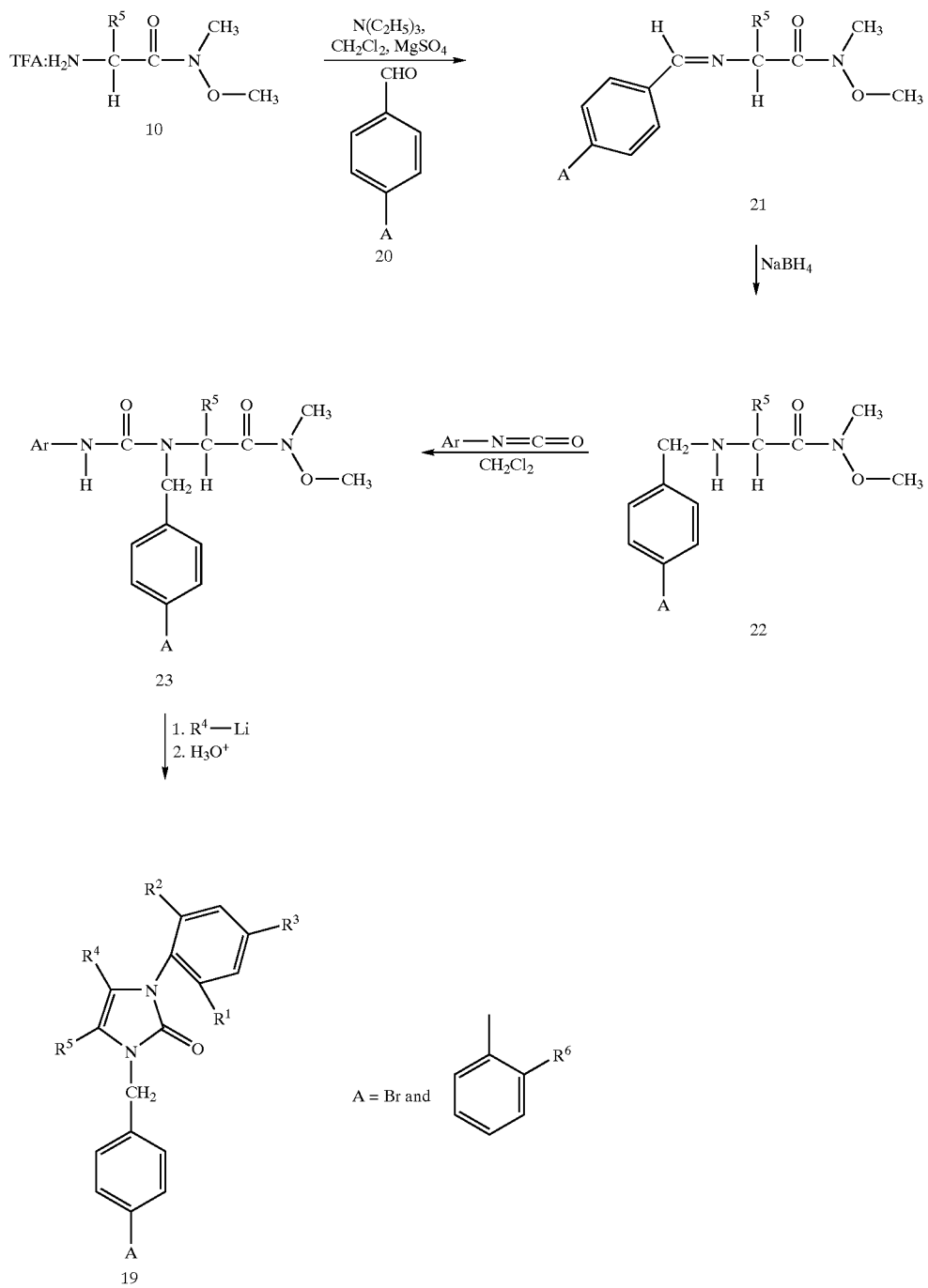

Scheme VII

Synthetic Scheme VII shows the preparation of substituted benzylimidazol-2-ones 19 from the TFA salt of the amino amide 10 (prepared in Scheme II). In step 1, the TFA salt 10 is allowed to react with the substituted benzaldehyde 20 in the presence of triethylamine and anhydrous magnesium sulfate to give the imine 21. In step 2, the imine 21 is allowed to react with sodium borohydride to give the substituted benzylamine 22. In step 3, the benzylamine 22 is allowed to react with the appropriate isocyanate 11 to give the substituted benzylurea 23. In step 4, the urea 23 is first allowed to react with an organolithium reagent $R^4$—Li (or lithium aluminum hydride (LAH) when $R^4$=H) and subsequently with dilute aqueous acid to give the desired substituted benzylimidazol-2-one 19.

Scheme VIII

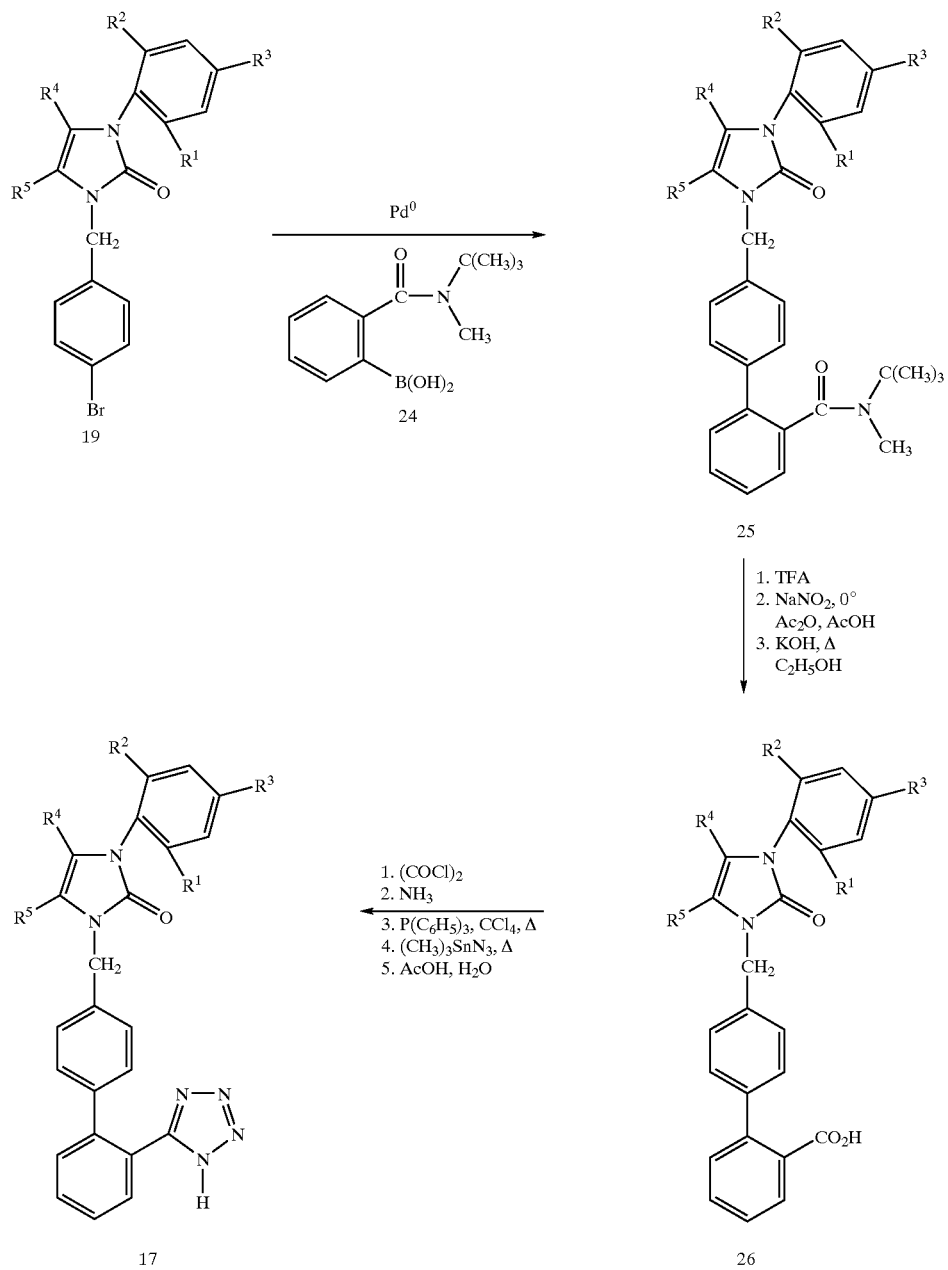

Synthetic Scheme VIII shows the preparation of biphenylmethylimidazol-2-ones 17 from 4-bromobenzylimidazol-2-ones 19 (prepared in Scheme VII). In step 1, the bromobenzylimidazol-2-one 19 is allowed to react with the boronic acid amide 24 (which can be prepared from N-t-butyl-N-methylbenzamide via ortho metalation) in the presence of a palladium catalyst, such as tetrakis(triphenylphospine) palladium, to give the biphenylmethylimidazol-2-one amide 25. In step 2, the N-t-butyl-N-methylamide 25 is allowed to react with TFA to give the N-methylamide, sodium nitrite to give the N-nitrosoamide, and ethanolic potassium hydroxide to give the biphenylmethylimidazol-2-one carboxylic acid 26. In step 3, the acid 26 is allowed to react with oxalyl chloride to give the acid chloride, anhydours ammonia to give the primary amide, triphenylphospine/carbon tetrachloride to give the nitrite, and acetic acid/water to give the desired angiotensin II antagonist 17.

The following Examples 1–9 contain detailed descriptions of the methods of preparation of compounds of Formula I. These detailed descriptions fall within the scope of, and serve to exemplify, the above described General Synthetic Procedures which form part of the invention. These detailed descriptions are presented for illustrative purposes only and are not intended as a restriction on the scope of the invention. All parts are by weight and temperatures are in degrees Centigrade, unless otherwise indicated.

EXAMPLE 1

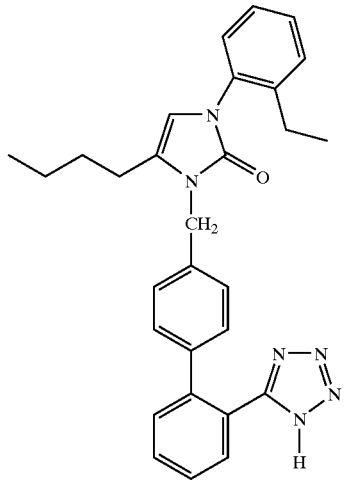

1-(2-ethylphenyl)-4-butyl-1,3-dihydro-3-[2'-(1H-tetrazol-5-yl)[1,1'-biphenyl]-4-ylmethyl]-2H-imidazol-2-one Step 1: Preparation of N-Triphenylmethyl-5-[2-(4'-bromomethylbiphen-2-yl]tetrazole.

A 542.5 g (2.4 mol) sample of methyl 2-(p-tolyl)benzoate (Chemo Dynamics Inc.) was dissolved in 5.5 L of ethanol and treated with 3 L (7.5 mol) of 2.5 N sodium hydroxide. The reaction was stirred overnight at ambient temperature and treated with an additional 480 ml (6.0 mol) of sodium hydroxide; stirring was continued for an additional 24 h and the ethanol removed in vacuo. The remaining solution was cooled in ice and acidified to pH 1 with hydrochloric acid which caused the product to precipitate; filtration and drying in vacuo gave 510 g (100%) of crude 2-(p-tolyl)benzoic acid: mp 145.0–147.5° C.; NMR (CDCl$_3$) δ 2.40 (s, 3H), 7.17–7.28 (m, 4H), 7.35–7.45 (m, 2H), 7.51–7.59 (m, 1H), 7.90–7.97 (m, 1H). The crude acid was suspended in 1 L of toluene and slowly treated with 400 g (3.15 mol) of oxalyl chloride under nitrogen. The reaction was allowed to stir at ambient temperature for 4.5 h and concentrated in vacuo to remove excess oxalyl chloride. The residue was redissolved in 2 L of toluene and treated with 92.8 g (5.46 mol) of anhydrous ammonia. The reaction was filtered and the filtrate concentrated in vacuo producing 424 g (84%) of crude 2-(p-tolyl)benzamide: mp 128–130° C.; NMR (CDCl$_3$) δ 2.40 (s, 3H), 5.28 (br s, 1H), 5.77 (br s, 1H), 7.21–7.53 (m, 7H), 7.76–7.83 (m, 1H). The crude amide was treated with 1420 ml (19.5 mol) of thionyl chloride at reflux for 3.5 h. The reaction was filtered and the thionyl chloride removed in vacuo. The residue was dissolved in 800 ml of toluene and reconcentrated in vacuo. On standing overnight, the residue crystallized. The crystals were collected and washed with hexane to give 296 g (64%) of 2-(p-tolyl)benzonitrile: mp 50.5–52.0° C.; NMR (CDCl$_3$) δ 2.42 (s, 3H), 7.22–7.34 (m, 2H), 7.37–7.52 (m, 3H), 7.58–7.66 (m, 1H), 7.72–7.78 (m, 1H). A 286 g (1.48 mol) sample of the crude nitrile was dissolved in 1630 mL to toluene and treated with 377 g (1.8 mol) of trimethyltinazide at reflux for 24 h. The reaction was cooled; filtration gave 600 g of crude N-trimethylstannyl-5-[2-(4'-methylbiphen-2-yl]tetrazole: mp 271–272° C. (dec.); NMR (DMSO-d$_6$) δ 0.36 (br t, J=34 Hz, 9H), 2.24 (s, 3H), 6.89–7.06 (m, 4H), 7.35–7.55 (m, 4H). The crude N-trimethylstannyl tetrazole was suspended in 4270 mL of toluene and 287 mL of anhydrous tetrahydrofuran (THF) and treated with 6.34 g (173 mol) of anhydrous hydrogen chloride at ambient temperature under nitrogen with stirring. The reaction was allowed to stand overnight and filtered; recrystallization from toluene gave 217 g (62%) of 5-[2-(4'-methylbiphen-2-yl)]tetrazole as a solid: mp 149–152° C.; NMR (DMSO-d$_6$) δ 2.28 (s, 3H), 6.94–7.02 (m, 2H), 7.08–7.15 (m, 2H), 7.50–7.59 (m, 2H), 7.62–7.72 (m, 2H). A 200 g (0.85 mol) sample of the tetrazole was suspended in 3.3 L of dichloromethane and treated with 262 g (0.91 mol) of triphenylmethyl chloride and 141 mL (1.0 mol) of anhydrous triethylamine. The reaction was stirred at reflux for 3 h under nitrogen, washed with water, dried (MgSO$_4$), and concentrated in vacuo. Recrystallization gave 338 g (83%) of N-triphenylmethyl-5-[2-4'-methylbiphen-2-yl)]tetrazole as a colorless solid: mp 170–173° C.; NMR (CDCl$_3$) δ 2.27 (s, 3H), 6.86–6.96 (m, 8H), 6.98–7.04 (m, 2H), 7.09–7.52 (m, 12H), 7.86–7.94 (m, 1H). The N-triphenylmethyl tetrazole was dissolved in 4260 mL of carbon tetrachloride and treated with 126.4 g (0.71 mol) of N-bromosuccinimide (NBS) of 11.9 g (49 mmol) of benzoyl peroxide at reflux for 3.5 h. The reaction was filtered and the solvent removed in vacuo. Recrystallization from toluene gave 277 g (59%) of N'triphenylmethyl-5-[2-4'-bromomethylbiphen-2-yl)]tetrazole as a colorless solid: mp 140–142° C.; NMR (CDCl$_3$) δ 4.39 (s, 2H), 6.85–6.95 (m, 7H), 7.06–7.15 (m, 4H), 7.22–7.43 (m, 9H), 7.45–7.55 (m, 2H), 7.94–8.01 (m, 1H). NMR indicated that this material was only 85% pure; it contained 7% of corresponding dibromocompound (δ 6.50) and 8% of starting material (δ 2.27); however, no further attempts at purification were made and this mixture was used as is for the subsequent alkylation reaction.

Step 2: Preparation of N-t-Boc-L-norleucine-N-methoxy-N-methylamide.

Under nitrogen, a stirred solution of 70.25 g (0.3 mol) of N-t-Boc-norleucine and 30.8 g (0.3 mol) of triethylamine (TEA) in 750 mL of dichloromethane (DCM) at −15° C. was treated with 44.2 g (0.32 mol) of isobutyl chloroformate. After 15 min, a slurry of 32.6 g (0.33 mol) of N,O-dimethylhydroxylamine in 100 mL of DCM was added followed by 33.8 g (0.33 mol) of TEA at such a rate as to maintain the reaction temperature at −5° C. The reaction was stirred at −10° C. for 1 h and then allowed to warm to ambient temperature and stir overnight. The reaction was diluted with 1 L of chloroform and washed with 1 M citric acid, NaHCO$_3$ (sat), and brine. The solution was dried (Na$_2$SO$_4$) and concentrated in vacuo to give 80.2 g of crude product as a yellow oil. Purification by silica gel chromatography (Waters Prep-500A) using ethyl acetate/hexane (75:25) gave 58.1 g (74%) of colorless product as an oil: NMR (CDCl$_3$) δ 0.88 (t, J=7 Hz, 3H), 1.28–1.38 (m, 4H), 1.43 (s, 9H), 1.49–1.57 (m, 1H), 1.63–1.75 (m, 1H), 3.20 (s, 3H), 3.76 (s, 3H), 4.60–4.72 (m, 1H), 5.13 (d, J=8 Hz, 1H).

Step 3: Preparation of L-norleucine-N-methoxy-N-methylamide.

Under nitrogen, 50 g (182 mmol) of N-t-Boc-L-norleucine-N-methoxy-N-methylamide from Step 2 was dissolved in 25 mL of methylene chloride and treated with 75 mL of anhydrous trifluoroacetic acid (TFA). The mixture was stirred at ambient temperature overnight and concentrated in vacuo. The residue was dissolved in 1 M Na$_2$CO$_3$ and continuously extracted with ether to afford 29.1 g (66%) of L-norleucine-N-methoxy-N-methylamide as a colorless oil: NMR (CDCl$_3$) δ 0.75 (s, 3H), 1.10–1.35 (m, 4H), 1.74–1.85 (m, 2H), 3.04 (s, 3H), 3.55 (s, 3H), 3.70–3.79 (m, 1H).

Step 4: Preparation of 1-(2-ethylphenyl)-4-butyl-1,3-dihydro-2H-imidazol-2-one.

Under nitrogen, a solution of 4.86 g (30 mmol) of carbonyl diimidazole in 50 mL of methylene chloride was treated with 3.63 g (30 mmol) of 2-ethylaniline (Aldrich). The reaction was allowed to stir at ambient temperature for 90 min prior to the addition of 4.80 g (30 mmol) of L-norleucine-N-methoxy-N-methylamide from Step 3. The reaction was stirred overnight, filtered and concentrated in vacuo. Purification by silica gel chromatography (Waters Prep-500A) using ethylacetate/hexane (40:60) gave 2.45 g (25%) of the 2-ethylphenyl urea of L-norleucine-N-methoxy-N-methylamide as a colorless solid: NMR (CDCl$_3$) δ 0.88 (t, J=7 Hz, 3H), 1.14 (t, J=8 Hz, 3H), 1.30–1.38 (m, 2H), 1.38–1.60 (m, 2H), 1.63–1.80 (m, 2H), 2.49 (t, J=7 Hz, 2H), 2.56 (t, J=8 Hz, 2H), 3.20 (s, 3H), 3.82 (s, 3H), 4.18–4.27 (m, 1H), 4.96 (5, J=8 Hz, 1H), 6.77 (br s, 1H), 7.05–7.22 (m, 2H), 7.32–7.43 (m, 1H), 7.54 (d, J=8 Hz, 1H). A solution of 2.37 g (7.4 mmol) of this urea in 50 mL of anhydrous THF/ether (1:1) was treated with 9.2 mL (9.2 mmol) of 1M LAH in ether at ambient temperature. The reaction was allowed to stir for 90 min and was slowly treated with a solution of 1.77 g (13 mmol) of KHSO$_4$ in 45 mL of water. This mixture was rapidly stirred for 3 hr and then the layers were separated. The aqueous layer was extracted three times with ether and the extracts were combined with the organic layer. The etheral solution was washed with brine, dried (MgSO$_4$), and concentrated in vacuo. The residue was dissolved in 30 mL of methylene chloride, treated with 0.5 mL of TFA, and stirred at reflux for 3 hr. The reaction was cooled to ambient temperature, washed with NaHCO$_3$ (sat), dried (MgSO$_4$), and concentrated in vacuo to give 1.8 g (100%) of 1-(2-ethylphenyl)-4-butyl-1,3-dihydro-2H-imidazol-2-one as a colorless oil: NMR (CDCl$_3$) δ0.92 (t, J=7 Hz, 3H), 1.17 (t, J=7, Hz, 3H), 1.38 (m, J=7 Hz, 2H), 1.58 (m, J=7 Hz, 2H), 2.46 (t, J=7 Hz, 2H), 2.58 (q, J=7 Hz, 2H), 6.06 (s, 1H), 7.16–7.30 (m, 2H), 7.30–7.40 (m, 2H).

Step 5: Preparation of 1-(2-ethylphenyl)-4-butyl-1,3-dihydro-3-[2'-(1H-tetrazol-5-yl)[1,1'-biphenyl]-4-ylmethyl]-2H-imidazol-2-one.

Under nitrogen, a solution of 1.8 g (7.4 mmol) of the imidazol-2-one from Step 4 in 75 mL of anhydrous dimethylforamide (DMF) was cooled to –63° C. (CHCl$_3$/CO$_2$) and treated with 7.4 mL (7.4 mmol) of 1 M potassium tert-butoxide in THF. The anion solution was then treated with 5.17 g (7.4 mmol) of solid N-triphenylmethyl-5-[(2-(4'bromomethylbiphen-2-yl]tetrazole from Step 1 at such a rate to maintain the reaction temperature below –55° C. After the addition was complete, the reaction was allowed to slowly warm to ambient temperature overnight, quench with 10 mL of water, and concentrated in vacuo. The residue was dissolved in ethyl acetate which was washed with water, dried (MgSO$_4$), and reconcentrated in vacuo to give the crude product. Purification by silica gel chromatography (waters Prep-500A) using ethyl acetate/hexane (30:70) gave 1.10 g (15%) of pure trityl-protected coupled product which was stirred in 20 mL of acetic acid/water (90:10) for 3 days. All volitiles were removed in vacuo and the residue recrystallized from acetonitrile to give 535 mg (73%) of 1-(2-ethylphenyl)-4-butyl-1,3-dihydro-3-[2'-(1H-tetrazol-5-yl)[1,1'-biphenyl]-4-ylmethyl]-2H-imidazol-2-one as a colorless solid: mp 188–189° C.; NMR (CDCl$_3$) δ0.82 (t, J=7 Hz, 3H), 0.97 (t, J=8 Hz, 3H), 1.23–1.35 (m, 2H), 1.36–1.48 (m, 2H), 2.26 (t, J=7 Hz, 2H), 2.37 (q, J=8 Hz, 2H), 4.75 (s, 2H), 5.95 (s, 1H), 6.98–7.15 (m, 7H), 7.36–7.58 (m, 4H), 7.79 (dd, J=8 and 2 Hz, 1H); MS (FAB) m/e (rel intensity) 479 (12), 277 (8), 243 (18), 185 (100), 149 (8); HRMS. Calc'd for M+H: 479.2560. Found: 479.2590.

EXAMPLE 2

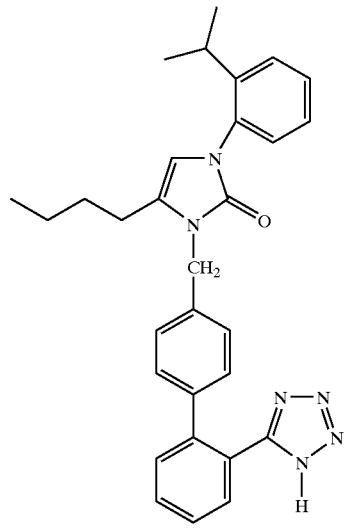

1-(2-isopropylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2-isopropylphenyl)-4-butyl-1,3-dihydro-2H-imidazol-2-one.

Following General Synthetic Scheme III, 1-(2-isopropylphenyl)-4-butyl-1,3-dihydro-2H-imidazol-2-one was prepared: NMR (CDCl$_3$) δ 0.89 (t, J=7 Hz, 3H), 1.21 (d, J=7 Hz, 6H), 1.30–1.44 (m, 2H), 1.48–1.60 (m, 2H), 2.38 (t, J=7 Hz, 2H), 3.05 (m, J=7 Hz, 1H), 5.93–5.96 (m, 1H), 7.17–7.42 (m, 4H), 10.65 (br s, 1H); MS (FAB) m/e (rel intensity) 259 (100); HRMS. Calc'd for M+H: 259.1810. Found: 259.1799.

Step 2: Preparation of 1-(2-isopropylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2-isopropylphenyl)-4-butyl-1,3-dihydro-3-[2'-(1H-tetrazol-5-yl)[1,1'-biphenyl]-4-ylmethyl]-2H-imidazol-2-one as a colorless solid: mp 167–168° C.; NMR (CDCl$_3$) δ 0.82 (t, J=7 Hz, 3H), 0.99 (d, J=8 Hz, 6H), 1.22–1.34 (m, 2H), 1.35–1.49 (m, 2H), 2.27 (t, J=7 Hz, 2H), 2.77 (m, J=8 Hz, 1H), 4.74 (s, 2H), 5.95 (s, 1H), 6.98 (d, J=3 Hz, 1H), 7.03 (d, J=8 Hz, 2H), 7.10 (d, J=8 Hz, 2H), 7.14–7.24 (m, 2H), 7.35–7.56 (m, 4H), 7.76 (d, J=8

Hz, 1H). MS (FAB) m/e (rel intensity) 493 (18), 207 (100), 178 (19), 130 (5); HRMS. Calc'd for M+H: 493.2716. Found: 493.2684.

EXAMPLE 3

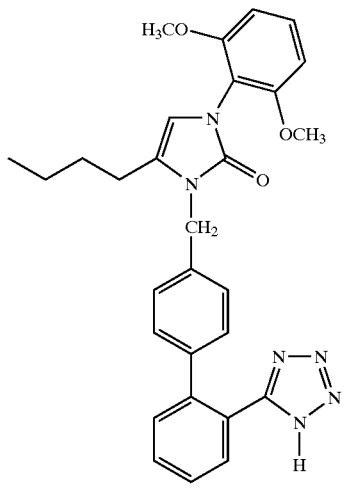

1-(2,6-dimethoxyphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,6-dimethoxyphenyl)-4-butyl-1,3-dihydro-2H-imidazol-2-one.

Following General Synthetic Scheme III, 1-(2,6-dimethylphenyl)-4-butyl-1,3-dihydro-2H-imidazol-2-one was prepared: NMR (DMSO-$d_6$) δ 0.89 (t, J=8 Hz, 3H), 1.27–1.40 (m, 2H), 1.42–1.57 (m, 2H), 2.26 (t, J=8 Hz, 2H), 3.71 (s, 6H), 5.91 (t, J=1 Hz, 1H), 6.72 (d, J=8 Hz, 2H), 7.31 (t, J=8 Hz, 2H), 9.85 (br s, 1H).

Step 2: Preparation of 1-(2,6-dimethoxyphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,6-dimethoxyphenyl)-4-butyl-1,3-dihydro-3-[2'-(1H-tetrazol-5-yl)[1,1'-biphenyl]-4-ylmethyl]-2H-imidazol-2-one as a colorless solid: mp 189–191° C. (dec); NMR (DMSO-$d_6$) δ 0.81 (t, J=7 Hz, 3H), 1.20–1.44 (m, 4H), 2.22 (t, J=7 Hz, 2H), 3.74 (s, 6H), 4.80 (s, 2H), 6.07 (s, 1H), 6.76 (d, J=8 Hz, 2H), 7.08 (d, J=8 Hz, 2H), 7.13 (d, J=8 Hz, 2H), 7.34 (t, J=8 Hz, 1H), 7.53–7.61 (m, 2H), 7.62–7.73 (m, 2H). MS (FAB) m/e (rel intensity) 511 (20); HRMS. Calc'd for M+H: 511.2458. Found; 511.2527.

EXAMPLE 4

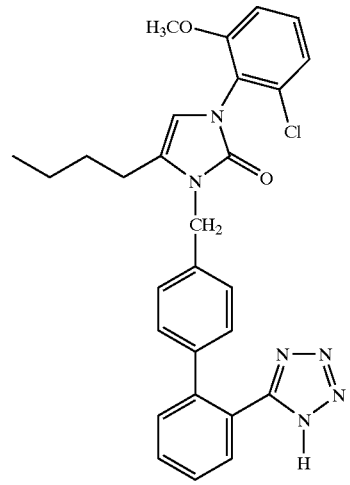

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2-chloro-6-methylphenyl)-4-butyl-1,3-dihydro-2H-imidazol-2-one.

Following General Synthetic Scheme III, 1-(2-chloro-6-methylphenyl)-4-butyl-1,3-dihydro-2H-imidazol-2-one was prepared: NMR (CDCl$_3$) δ 0.90 (t, J=7 Hz, 3H), 1.35 (m, J=7 Hz, 2H), 1.55 (m, J=7 Hz, 2H), 2.26 (s, 3H), 2.40 (t, J=7 Hz, 2H), 5.85–5.88 (m, 1H), 7.17–7.25 (m, 2H), 7.33 (dd, J=7 and 2 Hz, 1H), 10.20 (br s, 1H); MS (FAB) m/e (rel intensity) 265 (100), 249 (3), 221 (10), 201 (2), 187 (8); HMRS: Calc'd for M+H: 265.1108. Found: 265.1126.

Step 2: Preparation of 1-(2-chloro-6-methylphenyl)-4-butyl-1,3-dihydro-3-[2'-(1H-tetrazol-5-yl)[1,1'-biphenyl]-4-ylmethyl]-2H-imidazol-2-one.

Following Feneral Synthetic Scheme VI, the imidazol-2-one from Step 1 was converted to 1-(2-chloro-6-methylpheny)-4-butyl-1,3-dihydro-3-[2'-(1H-tetrazol-5-yl)[1,1'-biphenyl]-4-ylmethyl]-2H-imidazol-2-one as a colorless solid: mp 163–164° C.; NMR (CDCl$_3$) δ 0.83 (t, J=7 Hz, 3H), 1.21–1.35 (m, 2H), 1.36–1.50 (m, 2H), 2.03 (s, 3H), 2.26 (t, J=8 Hz, 2H), 4.68 (d, J=16 Hz, 1H), 4.87 (d, J=16 Hz, 1H), 6.94 (dd, J=7 and 2 Hz, 1H), 7.00–7.08 (m, 4H), 7.12–7.17 (m, 2H), 7.26–7.33 (m, 1H), 7.40–7.51 (m, 2H), 7.54–7.61 (m, 2H), 7.77 (dd, J=8 and 1 Hz, 1H); MS (FAB) m/e (rel intensity) 499 (15), 456 (3), 265 (4), 207 (100), 192 (24), 178 (21); HRMS: Calc'd for M+H: 499.2013. Found 499.2011.

EXAMPLE 5

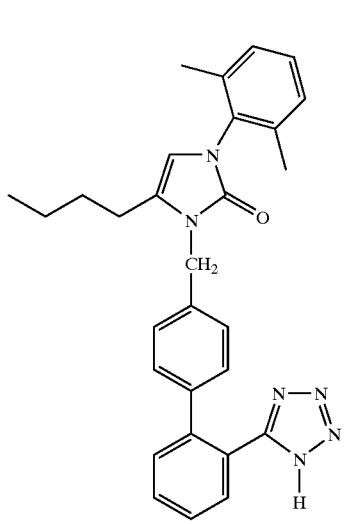

1-(2,6-dimethylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,6-dimethylphenyl)-4-butyl-1,3-dihydro-2H-imidazol-2-one.

Following General Synthetic Scheme III, 1-(2,6-dimethylphenyl)-4-butyl-1,3-dihydro-2H-imidazol-2-one was prepared: NMR (CDCl$_3$) δ 0.91 (t, J=7 Hz, 3H), 1.29–1.32 (m, 2H), 1.49–1.61 (m, 2H), 2.18 (s, 6H), 2.41 (t, J=7 Hz, 2H), 5.83–5.86 (m, 1H), 7.07–7.21 (m, 3H), 9.66 (br s, 1H); MS (FAB) m/e (rel intensity) 245 (100), 215 (4), 118 (9); HMRS: Calc'd for M+H: 245.1654. Found 245.1668.

Step 2: Preparation of 1-(2,6-dimethylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,6-dimethylphenyl)-4-butyl-1,3-dihydro-3-[2'-(1H-tetrazol-5-yl)[1,1'-biphenyl]-4-ylmethyl]-2H-imidazol-2-one as a colorless solid: mp 177–178° C. (dec); NMR (CDCl$_3$) δ 0.83 (t, J=8 Hz, 3H), 1.22–1.33 (m, 2H), 1.34–1.47 (m, 2H), 1.92 (s, 6H), 2.25 (t, J=8 Hz, 2H), 4.76 (s, 2H), 5.82 (s, 1H), 6.76 (d, J=8 Hz, 2H), 6.96 (t, J=8 Hz, 1H), 7.04 (d, J=8 Hz, 2H), 7.15 (d, J=8 Hz, 2H), 7.42–7.62 (m, 3H), 7.74 (dd, J=8 and 2 Hz, 1H); MS (FAB) m/e (rel intensity) 479 (23), 207 (60); HRMS. Calc'd for M+H: 479.2559. Found: 479.2500.

EXAMPLE 6

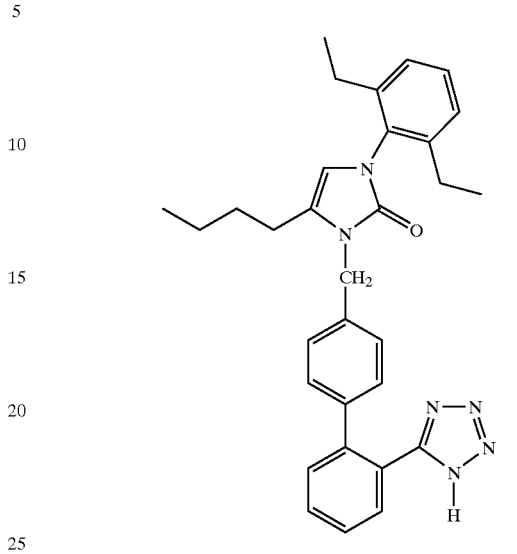

1-(2,6-diethylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,6-diethylphenyl)-4-butyl-1,3-dihydro-2H-imidazol-2-one.

Following General Synthetic Scheme III, 1-(2,6-diethylphenyl)-4-butyl-1,3-dihydro-2H-imidazol-2-one was prepared: NMR (CDCl$_3$) δ 0.89 (t, J=7 Hz, 3H), 1.17 (t, J=7 Hz, 6H), 1.33 (m, J=7 Hz, 2H), 1.53 (m, J=8 Hz, 2H), 2.40 (t, J=7 Hz, 2H), 2.50 (q, J=8 Hz, 2H), 2.52 (q, J=8 Hz, 2), 5.82–5.84 (m, 1H), 7.16 (d, J=8 Hz, 2H), 7.26–7.33 (m, 1H), 10.71 (br s, 1H); MS (FAB) m/e (rel intensity) 273 (100), 255 (15); HRMS: Calc'd for M+H: 273.1967. Found: 273.1980.

Step 2: Preparation of 1-(2,6-diethylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,6-diethylphenyl)-4-butyl-1,3-dihydro-3-[2'-(1H-tetrazol-5-yl)[1,1'-biphenyl]-4-ylmethyl]-2H-imidazol-2-one as a colorless solid: mp 198–200° C. (dec); NMR (CDCl$_3$) δ 0.83 (t, J=7 Hz, 3H), 0.95 (t, J=8 Hz, 6H) 1.22–1.34 (m, 2H), 1.35–1.48 (m, 2H), 2.20–2.32 (m, 6H), 4.75 (s, 2H), 5.85 (s, 1H) 6.84 (d, J=8 Hz, 2H), 7.02 (d, J=8 Hz, 2H), 7.10 (t, J=8 Hz, 1H), 7.15 (d, J=8 Hz, 2H), 7.41–7.53 (m, 2H), 7.54–7.61 (m, 1H), 7.71 (d, J=8 Hz, 1H); MS (FAB) m/e (rel intensity) 507 (100), 479 (6), 464 (10); HRMS: Calc'd for M+H: 507.2872. Found: 507.2853.

EXAMPLE 7

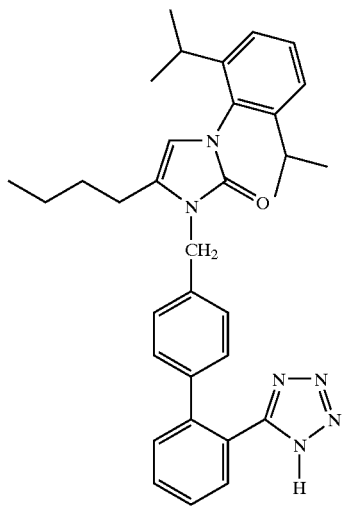

1-(2,6-diisopropylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,6-diisopropylphenyl)-4-butyl-1,3-dihydro-2H-imidazol-2-one.

Following General Synthetic Scheme III, 1-(2,6-diisopropylphenyl)-4-butyl-1,3-dihydro-2H-imidazol-2-one was prepared: NMR (CDCl₃) δ 0.92 (t, J=8 Hz, 3H), 1.16 (d, J=8 Hz, 6H), 1.23 (d, J=8 Hz, 6H), 1.29–1.44 (m, 2H), 1.50–1.61 (m, 2H), 2.41 (t, J=8 Hz, 2H), 2.75–2.91 (m, 2H), 5.85 (t, J=1 Hz, 1H), 7.22 (d, J=8 Hz, 2H), 7.36 (t, J=8 Hz, 1H).

Step 2: Preparation of 1-(2,6-diisopropylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,6-diisopropylphenyl)-4-butyl-1,3-dihydro-3-[2'-(1H-tetrazol-5-yl)[1,1'-biphenyl]-4-ylmethyl]-2H-imidazol-2-one as a colorless solid: mp 202–203° C. (dec); NMR (CDCl₃) δ 0.86 (t, J=7 Hz, 3H), 0.99 (d, J=7 Hz, 6H), 1.08 (d, J=7 Hz, 6H), 1.25–1.52 (m, 4H), 2.32 (t, J=8 Hz, 2H), 2.63 (m, J=7 Hz, 2H), 4.75 (s, 2H), 5.90 (s, 1H), 7.01–7.12 (m, 6H), 7.29 (t, J=8 Hz, 1H), 7.37–7.48 (m, 2H), 7.54 (dt, J=8 and 2 Hz, 1H), 7.70 (dd, J=8 and 2 Hz, 1H); MS (FAB) m/e (rel intensity) 535 (22), 207 (100), 178 (33); HRMS. Calc'd for M+H: 535.3185. Found: 535.3168.

EXAMPLE 8

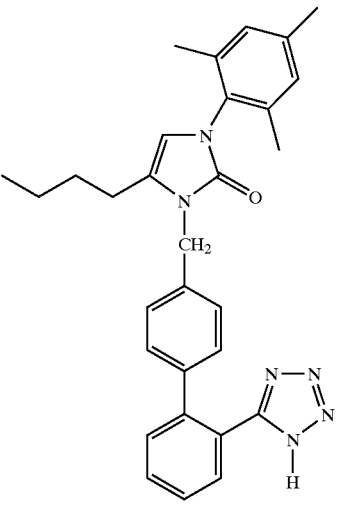

1-(2,4,6-trimethylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,4,6-trimethylphenyl)-4-butyl-1,3-dihydro-2H-imidazol-2-one.

Following General Synthetic Scheme III, 1-(2,4,6-trimethylphenyl)-4-butyl-1,3-dihydro-2H-imidazol-2-one was prepared: NMR (CDCl₃) δ 0.91 (t, J=8 Hz, 3H), 1.28–1.42 (m, 2H), 1.47–1.60 (m, 2H), 2.14 (s, 6H), 2.30 (s, 3H), 2.40 (t, J=8 Hz, 2H), 5.80–5.83 (m, 1H), 6.93 (s, 2H), 10.20 (br s, 1H).

Step 2: Preparation of 1-(2,4,6-trimethylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,4,6-trimethylphenyl)-4-butyl-1,3-dihydro-3-[2'-(1H-tetrazol-5-yl)[1,1'-biphenyl]-4-ylmethyl]-2H-imidazol-2-one as a colorless solid: mp 187–188° C. (dec); NMR (CDCl₃) δ 0.82 (t, J=7 Hz, 3H), 1.21–1.34 (m, 2H), 1.35–1.46 (m, 2H), 1.87 (s, 6H), 2.19 (s, 3H), 2.24 (t, J=8 Hz, 2H), 4.76 (s, 2H), 5.79 (s, 1H), 6.54 (s, 2H), 7.08 (d, J=8 Hz, 2H), 7.17 (d, J=8 Hz, 2H), 7.44–7.63 (m, 3H), 7.77 (dd, J=8 and 2 Hz, 1H); MS (FAB) m/e (rel intensity) 493 (15), 207 (100), 178 (18); HRMS. Calc'd for M+H: 493.2716. Found: 493.2694.

EXAMPLE 9

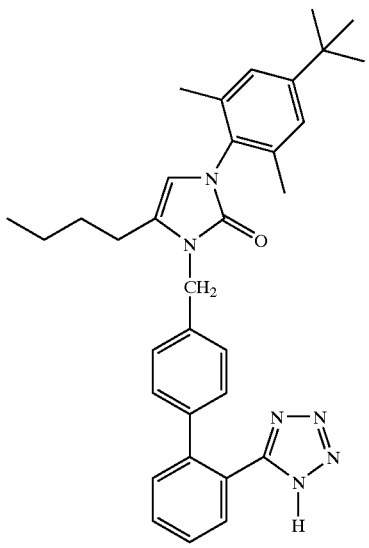

1-(2,6-dimethyl-4-tertbutylphenyl)-4-butyl-1,3-dihydro-3-[2'-(1H-tetrazol-5-yl)[1,1'-biphenyl]-4-ylmethyl]-2H-imidazol-2-one Step 1: Preparation of 1-(2,6-dimethyl-4-tertbutylphenyl)-4-butyl-1,3-dihydro-2H-imidazol-2-one.

Following General Synthetic Scheme III, 1-(2,6-dimethyl-4-tertbutylphenyl)-4-butyl-1,3-dihydro-2H-imidazol-2-one was prepared: NMR (CDCl$_3$) δ 0.90 (t, J=8 Hz, 3H), 1.26–1.42 (m, 2H), 1.30 (s, 9H), 1.48–1.60 (m, 2H), 2.18 (s, 6H), 2.40 (t, J=8 Hz, 2H), 5.83 (s, 1H), 7.11 (s, 2H), 10.30 (br s, 1H).

Step 2: Preparation of 1-(2,6-dimethyl-4-tertbutylphenyl)-4-butyl-1,3-dihydro-3-[2'-(1H-tetrazol-5-yl)[1,1'-biphenyl]-4-ylmethyl]-2H-imidazol-2-one.

Following General Synthetic Scheme VI, the imidazol-2-one from Step 1 was converted to 1-(2,6-dimethyl-4-tertbutylphenyl)-4-butyl-1,3-dihydro-3-[2'-(1H-tetrazol-5-yl)[1,1'-biphenyl]-4-ylmethyl]-2H-imidazol-2-one as a colorless solid: mp 134–135° C.; NMR (CDCl$_3$) δ 0.85 (t, J=7 Hz, 3H) 1.23–1.51 (m, 4H), 1.28 (s, 9H), 1.94 (s, 6H), 2.30 (t, J=8 Hz, 2H), 4.79 (s, 2H), 5.87 (s, 1H), 6.98 (d, J=9 Hz, 4H), 7.07 (d, J=9 Hz, 2H), 7.38–7.44 (m, 1H), 7.47–7.53 (m, 1H), 7.54–7.62 (m, 1H), 7.80 (d, J=8 Hz, 1H); MS (FAB) m/e (rel intensity) 535 (19), 207 (100), 178 (31); HRMS. Calc'd for M+H: 535.3185. Found: 535.3192.

Biological Evaluation

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [Endocrinology, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 10$^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded (3×10$^{-10}$ to 1×10$^{-5}$ M). Each concentration of AII was allowed to elicit its maximal contraction, and then AII was washed out repeatedly for 30 minutes before rechallenging with a higher concentration of AII. Aorta rings were exposed to the test antagonist at 10$^{-5}$ M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [Br. J. Pharmacol. Chemother., 2, 189–206 (1947)]. The pA$_2$ value is the concentration of the antagonist which increases the EC$_{50}$ value for AII by a factor of two. Each test antagonist was evaluated in aorta rings from two rabbits. Results are reported in Table I.

Assay C: In Vivo Intragastric Pressor Assay Response for AII Antagonists

Male Sprague-Dawley rats weighing 225–300 grams were anesthetized with methohexital (30 mg/kg, i.p.) and catheters were implanted into the femoral artery and vein. The catheters were tunneled subcutaneously to exit dorsally, posterior to the head and between the scapulae. The catheters were filled with heparin (1000 units/ml of saline). The rats were returned to their cage and allowed regular rat chow and water ad libitum. After full recovery from surgery (3–4 days), rats were placed in Lucite holders and the arterial line was connected to a pressure transducer. Arterial pressure was recorded on a Gould polygraph (mmHg). Angiotensin II was administered as a 30 ng/kg bolus via the venous catheter delivered in a 50 µl volume with a 0.2 ml saline flush. The pressor response in mm Hg was measured by the difference from pre-injection arterial pressure to the maximum pressure achieved. The AII injection was repeated every 10 minutes until three consecutive injections yielded responses within 4 mmHg of each other. These three responses were then averaged and represented the control response to AII. The test compound was suspended in 0.5% methylcellulose in water and was administered by gavage. The volume administered was 2 ml/kg body weight. The standard dose was 3 mg/kg. Angiotensin II bolus injections were given at 30, 45, 60, 75, 120, 150, and 180 minutes after gavage. The pressor response to AII was measured at each time point. The rats were then returned to their cage for future testing. A minimum of 3 days was allowed between tests. Percent inhibition was calculated for each time point following gavage by the following formula: [(Control Response−Response at time point)/Control Response]×100. Results are shown in Table I.

TABLE I

In Vitro and In Vivo Angiotensin II
Activity of Compounds of the Invention

| Test Compound Example # | [1]Assay A $IC_{50}$ (nM) | [2]Assay B $pA_2$ | [3]Assay C Dose: 3 mg/kg (i.g.) Inhibition (%) Duration (min.) |
|---|---|---|---|
| 1 | 14 | NC | 20%/— |
| 2 | 97 | NC | 70%/>180 min. |
| 3 | 9.8 | 8.53/8.61 | 25%/>180 min. |
| 4 | 13 | 9.06/8.85 | 35%/>180 min. |
| 5 | 6.3 | 9.07/— | 40%/>180 min. |
| 6 | 33 | 8.71/8.64 | <20% |
| 7 | 190 | —/6.54 | NT |
| 8 | 30 | 8.49/8.51 | 50%/>180 min. |
| 9 | 270 | 8.06/8.25 | NT |

[1]Assay A: Angiotensin II Binding Activity
[2]Assay B: In Vitro Vascular Smooth Muscle Response
[3]Assay C: In Vivo Pressor Response (all test compounds administered intragastrically at 3 mg/kg).
*NC = Non-competitive Antagonist
*NT = Not Tested Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a circulatory disorder or circulatory-related disorders, said method comprising administering to a subject susceptible to or afflicted with such disorder a therapeutically-effective amount of a compound selected from the group consisting of 1-(2-ethylphenyl)-4-butyl-1,3-dihydro-3-[2'-(1H-tetrazol-5-yl)[1,1'-biphenyl]-4-ylmethyl]-2H-imidazol-2-one;

1-(2-isopropylphenyl)-4-butyl-1,3-dihydro-3-[2'-(1H-tetrazol-5-yl)[1,1'-biphenyl]-4-ylmethyl]-2H-imidazol-2-one;

1-(2,6-dimethoxyphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one;

1-(2,6-dimethylphenyl)-4-butyl-1,3-dihydro-3-[2'-(1H-tetrazol-5-yl)[1,1'-biphenyl]-4-ylmethyl]-2H-imidazol-2-one;

1-(2,6-diethylphenyl)-4-butyl-1,3-dihydro-3-[2'-(1H-tetrazol-5-yl)[1,1'-biphenyl]-4-ylmethyl]-2H-imidazol-2-one;

1-(2,4,6-trimethylphenyl)-4-butyl-1,3-dihydro-3-[2'-(1H-tetrazol-5-yl)[1,1'-biphenyl]-4-ylmethyl]-2H-imidazol-2-one; and a pharmaceutically-acceptable salt thereof.

2. The method of claim 1 wherein said circulatory disorder or circulatory-related disorders is a cardiovascular disorder.

3. The method of claim 2 wherein said cardiovascular disorder is hypertension.

4. The method of claim 2 wherein said cardiovascular disorder is congestive heart failure.

5. The method of claim 2 wherein said cardiovascular disorder is arteriosclerosis.

6. A therapeutic method for treating glaucoma disorder mediated by angiotensin II receptors, said method comprising administering to a subject susceptible to or afflicted with said disorder a therapeutically effective amount of a compound selected from the group consisting of 1-(2-ethylphenyl)-4-butyl-1,3-dihydro-3-[2'-(1H-tetrazol-5-yl)[1,1'-biphenyl]-4-ylmethyl]-2H-imidazol-2-one;

1-(2-isopropylphenyl)-4-butyl-1,3-dihydro-3-[2'-(1H-tetrazol-5-yl)[1,1'-biphenyl]-4-ylmethyl]-2H-imidazol-2-one;

1-(2,6-dimethoxyphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one;

1-(2,6-dimethylphenyl)-4-butyl-1,3-dihydro-3-[2'-(1H-tetrazol-5-yl)[1,1'-biphenyl]-4-ylmethyl]-2H-imidazol-2-one;

1-(2,6-diethylphenyl)-4-butyl-1,3-dihydro-3-[2'-(1H-tetrazol-5-yl)[1,1'-biphenyl]-4-ylmethyl]-2H-imidazol-2-one;

1-(2,4,6-trimethylphenyl)-4-butyl-1,3-dihydro-3-[2'-(1H-tetrazol-5-yl)[1,1'-biphenyl]-4-ylmethyl]-2H-imidazol-2-one; and a pharmaceutically-acceptable salt thereof.

7. A therapeutic method for treating or preventing surgically-induced disorder, said method comprising administering to a subject susceptible to or afflicted with said disorder a therapeutically effective amount of a compound selected from the group consisting of 1-(2-ethylphenyl)-4-butyl-1,3-dihydro-3-[2'-(1H-tetrazol-5-yl)[1,1'-biphenyl]-4-ylmethyl]-2H-imidazol-2-one;

1-(2-isopropylphenyl)-4-butyl-1,3-dihydro-3-[2'-(1H-tetrazol-5-yl)[1,1'-biphenyl]-4-ylmethyl]-2H-imidazol-2-one;

1-(2,6-dimethoxyphenyl)-4-butyl-1,3-dihydro-3-[2'-(1H-tetrazol-5-yl)[1,1'-biphenyl]-4-ylmethyl]-2H-imidazol-2-one;

1-(2-chloro-6-methylphenyl)-4-butyl-1,3-dihydro-3-[2'-(1H-tetrazol-5-yl)[1,1'-biphenyl]-4-ylmethyl]-2H-imidazol-2-one;

1-(2,6-dimethylphenyl)-4-butyl-1,3-dihydro-3-[2'-(1H-tetrazol-5-yl)[1,1'-biphenyl]-4-ylmethyl]-2H-imidazol-2-one;

1-(2,6-diethylphenyl)-4-butyl-1,3-dihydro-3-[2'-(1H-tetrazol-5-yl)[1,1'-biphenyl]-4-ylmethyl]-2H-imidazol-2-one;

1-(2,4,6-trimethylphenyl)-4-butyl-1,3-dihydro-3-[2'-(1H-tetrazol-5-yl)[1,1'-biphenyl]-4-ylmethyl]-2H-imidazol-2-one; and a pharmaceutically-acceptable salt thereof.

8. The method of claim 7 wherein said method is for preventing post-angioplasty re-stenosis.

9. The method of claim 7 wherein said method is for treating coronary hypertrophy arising from aortal stenosis.

* * * * *